US011299513B2

United States Patent
Ramaseshan et al.

(10) Patent No.: US 11,299,513 B2
(45) Date of Patent: Apr. 12, 2022

(54) CYCLATIVE RELEASE OF PEPTIDIC COMPOUNDS

(71) Applicant: CIRCLE PHARMA, INC., South San Francisco, CA (US)

(72) Inventors: Mahesh Ramaseshan, South San Francisco, CA (US); Andrew Bockus, South San Francisco, CA (US)

(73) Assignee: CIRCLE PHARMA, INC., South San Francisco, CA (US)

( * ) Notice: Subject to any disclaimer, the term of this patent is extended or adjusted under 35 U.S.C. 154(b) by 0 days.

(21) Appl. No.: 16/633,969

(22) PCT Filed: Jul. 27, 2018

(86) PCT No.: PCT/US2018/044182
§ 371 (c)(1),
(2) Date: Jan. 24, 2020

(87) PCT Pub. No.: WO2019/023634
PCT Pub. Date: Jan. 31, 2019

(65) Prior Publication Data
US 2020/0207803 A1   Jul. 2, 2020

Related U.S. Application Data

(60) Provisional application No. 62/538,477, filed on Jul. 28, 2017.

(51) Int. Cl.
| C07K 1/04  | (2006.01) |
| C07K 1/107 | (2006.01) |
| C07K 7/64  | (2006.01) |

(52) U.S. Cl.
CPC .............. *C07K 1/042* (2013.01); *C07K 1/107* (2013.01); *C07K 7/64* (2013.01)

(58) Field of Classification Search
CPC ........... C07K 1/042; C07K 1/107; C07K 7/64
See application file for complete search history.

(56) References Cited

U.S. PATENT DOCUMENTS

| 9,376,465 B2    | 6/2016  | McInnes et al. |
| 2003/0036628 A1 | 2/2003  | Zheleva et al. |
| 2004/0053849 A1 | 3/2004  | Bair et al.    |
| 2004/0077549 A1 | 4/2004  | Bair et al.    |
| 2005/0153894 A1 | 7/2005  | Zheleva et al. |
| 2014/0296484 A1 | 10/2014 | McInnes et al. |
| 2017/0218018 A1 | 8/2017  | McInnes et al. |

FOREIGN PATENT DOCUMENTS

| GB | 2369823 A      | 6/2002  |
| JP | 2004269357 A   | 9/2004  |
| WO | WO-01/40142    | 6/2001  |
| WO | WO-02/50102    | 6/2002  |
| WO | WO-2005/040802 | 5/2005  |
| WO | WO-2006/105386 | 10/2006 |
| WO | WO-2008/000870 | 1/2008  |
| WO | WO-2010/080819 | 7/2010  |
| WO | WO-2015/048477 | 4/2015  |
| WO | WO-2017/046215 | 3/2017  |
| WO | WO-2017/046219 | 3/2017  |
| WO | WO-2017/046226 | 3/2017  |
| WO | WO-2017/046227 | 3/2017  |
| WO | WO-2017/046228 | 3/2017  |
| WO | WO-2017/046229 | 3/2017  |

OTHER PUBLICATIONS

Zhang et al (Tetrahedron Letters, 1997, vol. 38, No. 25, 4375-4378) (Year: 1997).*
U.S. Appl. No. 10/024,935, filed Jul. 17, 2018, Ham.
Andrews et al., "Design, synthesis, biological activity and structural analysis of cyclic peptide inhibitors targeting the substrate recruitment site of cyclin-dependent kinase complexes," Org. Biomol. Chem., 2, pp. 2735-2741 (2004).
Clark et al., "Solid-phase synthesis of backbone-cyclized β-helical peptides," Tetrahedron, 62(41), pp. 9533-9540 (2006).
Dai et al., "A novel CyclinE/CyclinA-CDK Inhibitor targets p27$^{Kip1}$ degradation, cell cycle progression and cell survival: Implications in cancer therapy," Cancer Letters, 333, pp. 103-112(2013).
International Search Report and Written Opinion for International Patent Application No. PCT/US2018/044182, dated Oct. 19, 2018 (11 pages).
Kontopidis et al., "Insights into Cyclin Groove Recognition: Complex Crystal Structures and Inhibitor Design through Ligand Exchange," Structure, 11, pp. 1537-1546 (2003).
Kontopidis et al., "Truncation and Optimisation of Peptide Inhibitors of Cyclin-Dependent Kinase 2-Cyclin A Through Structure-Guided Design," ChemMedChem, 4, pp. 1120-1128 (2009).
Liu et al., "Optimization of non-ATP competitive CDK/cyclin groove Inhibitors through REPLACE mediated Fragment Assembly," Author Manuscript, published in final edited form as: J. Med. Chem., 56(4), pp. 1573-1582 (2013).
Marsault et al., "Efficient parallel synthesis of macrocyclic peptidomimetics," Bioorg. Med. Chem. Lett., 18(16), pp. 4731-4735 (2008).
McInnes et al., "Peptidomimetic Design of CDK Inhibitors Targeting the Recruitment Site of the Cyclin Subunit," Curr. Med. Chem.—Anti-Cancer Agents, 3, pp. 57-69 (2003).
Ollivier et al., "Fmoc Solid-Phase Synthesis of Peptide Thioesters Using an Intramolecular N,S-Acyl Shift," Organic Letters, 7(13), pp. 2647-2650 (2005).
Premnath et al., "Benzamide capped peptidomimetics as Non-ATP competitive inhibitors of CDK2 using the REPLACE Strategy," Author Manuscript, published in final edited form as: Bioorg. Med. Chem. Lett., 26(15), pp. 3754-3760 (2016).

(Continued)

*Primary Examiner* — Sudhakar Katakam
(74) *Attorney, Agent, or Firm* — Mintz, Levin, Cohn, Ferris, Glovsky and Popeo, P.C.

(57) ABSTRACT

The present disclosure provides efficient and reliable methods for preparing cyclized peptidic compounds. Advantageously, the currently described methods allow for on-resin cyclization using a limited number of processing steps, while increasing the chemical diversity available for the cyclized peptidic compounds produced.

26 Claims, No Drawings

(56) References Cited

OTHER PUBLICATIONS

Premnath et al., "Development of Inhibitors of Protein-protein Interactions through REPLACE: Application to the Design and Development Non-ATP Competitive CDK Inhibitors," Journal of Visualized Experiments, 104, e52441, 16 pages (2015).
Premnath et al., "Fragment based discovery of Arginine isosteres through REPLACE: towards non-ATP competitive CDK inhibitors," Author Manuscript, published in final edited form as: Bioorg. Med. Chem., 22(1), pp. 616-622 (2014).
Premnath et al., "Iterative Conversion of Cyclin Binding Groove Peptides into Druglike CDK Inhibitors with Antitumor Activity," J. Med. Chem., 58, pp. 433-442 (2015).
Rezai et al., "Conformational Flexibility, Internal Hydrogen Bonding, and Passive Membrane Permeability: Successful in Silico Prediction of the Relative Permeabilities of Cyclic Peptides," J. Am. Chem. Soc., 128(43), pp. 14073-14080 (2006).
Yang and Moriello, "Solid phase synthesis of 'head-to-tail' cyclic peptides using a sulfonamide 'safety-catch' linker: the cleavage by cyclization approach," Tetrahedron Letters, 40, pp. 8197-8200 (1999).
Zhang and Tam, "Lactone and Lactam Library Synthesis by Silver Ion-Assisted Orthogonal Cyclization of Unprotected Peptides," J. Am. Chem. Soc., 121(14), pp. 3311-3320 (1999).
Zheleva et al., "Highly potent p21$^{WAF1}$-derived peptide inhibitors of CDK-mediated pRb phosphorylation: Delineation and structural insight into their interactions with cyclin A," J. Peptide Res., 60, pp. 257-270 (2002).
Zorzi et al., "Cyclic Peptide Therapeutics: Past, Present and Future," Curr. Opin. Biol., 38, pp. 24-29 (2017).

* cited by examiner

CYCLATIVE RELEASE OF PEPTIDIC COMPOUNDS

CROSS-REFERENCES TO RELATED APPLICATIONS

This application claims priority to U.S. Provisional Application No. 62/538,477, filed Jul. 28, 2017, which is incorporated herein in its entirety for all purposes.

BACKGROUND OF THE INVENTION

The vast majority of currently marketed drugs as well as drugs in development are small molecules or biologics. Although both small molecules and biologics provide significant healthful benefit, both classes of drugs only access a small fraction of possible drug targets. For instance, it is believed that small molecules target only 10% of proteins having a discrete hydrophobic pocket, and biologics target only 10% of targets that are integral to the membrane or outside the cell (Kotz, J. SciBX 5(45) (2012)). Thus, 80% of targets are inaccessible to the currently employed drug classes. One particularly difficult drug target of known biological importance is the disruption and modification of protein-protein interactions. Small molecules often lack the necessary size to disrupt protein-protein interactions, and biologics generally exhibit poor cell permeability and consequently cannot target intracellular protein-protein interactions. Unlike small molecules and biologics, cyclic peptides are a relatively unexplored area of drug candidates. Generally, cyclic peptides are 500-2,000 Da in size—larger than small molecules, yet smaller than biologics. At this size, cyclic peptides do not rely on a single hydrophobic pocket for target binding, have the potential to permeate the cell membrane, and provide the opportunity to open up vast new therapeutic real estate.

Despite the clinical promise of cyclic peptides, a major limitation to the large scale use of cyclic peptides in drug development is increasing their cell permeability. Indeed, almost all late stage and clinical stage cyclic peptides target extracellular peptides. (*Current Opinion in Chemical Biology* 2017, 38, 24-29.)

The cell permeability of cyclic peptides are known to rely on a number of factors including conformational flexibility and internal hydrogen bonding (Rezai et al., *J. Am. Chem. Soc.*, 128 (43):14073-14080 (2006)). Particularly useful tools to improve cell membrane permeability are selective N-methylation of the peptide backbone to shield polar groups and the use of peptoid-peptide hybrids. Incorporating peptoids (N-substituted glycines) into the cyclic peptide backbone provides both shielding of the polar backbone nitrogen and greater chemical diversity.

Despite known techniques to improve cell membrane permeability, current synthetic chemistry limits the ability to produce and test these potentially useful compounds. For example, protocols that require solid-phase peptide synthesis, cleavage, and solution phase cyclization require too many processing and handling steps for large scale compound screening that is necessary in drug development. More automated synthesis protocols are enabled by methods that allow for on-resin cyclization, thus avoiding separate solution phase cyclization steps. However, existing methods for on-resin cyclization based on cyclative release (i.e., simultaneous on-resin peptide cyclization and release) require BOC chemistry, which employs tert-butyloxycarbonyl protecting groups, for linear peptide assembly. BOC chemistry requires an acid deprotection step after the addition of each amino acid, and is thus incompatible with acid-sensitive residues such as N-methyl amino acids and peptoids (N-substituted glycines). As discussed above, N-methylation and the incorporation of peptoids into the cyclic peptide backbone are two key strategies to improving cell membrane permeability and chemical diversity. Thus, currently available methods for synthesizing cyclic peptides do not provide an effective means for preparing cyclic peptide compound libraries with the cell membrane permeability required to address intracellular therapeutic targets, and in particular there is a need for chemistry processes that are compatible with on-resin cyclization and process automation.

Comparatively, solid-phase Fmoc chemistry—a technique that uses the base labile fluorenylmethyloxycarbonyl or Fmoc protecting group—avoids the multiple acid deprotection steps required in BOC chemistry and does not cleave N-methyl amino acids or peptoids. Linear peptide synthesis with Fmoc chemistry is, however, incompatible with any known on-resin peptide cyclization techniques. While cyclic peptides have been synthesized via cyclative release using the Fmoc strategy and Kenner's safety catch linkers, the application to high-throughput synthesis is limited due to lower yields of cyclic peptides resulting from insufficient activation of the acylsulfanomide bond. (Lihu Yang, Greg Moriello, Tetrahedron Letters, 40 (1999), 8197-8200).

As such, there is a need in the art for synthetic methods for preparing cyclic peptides with improved cell membrane permeability and greater chemical diversity. The present invention addresses this need and provides related advantages as well.

BRIEF SUMMARY OF THE INVENTION

In one aspect, provided herein is a method for preparing a cyclized peptidic compound of Formula I:

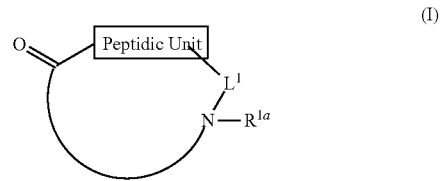

the method comprising
forming a cyclization reaction mixture comprising a thiophilic catalyst, a non-nucleophilic base, and a compound of Formula II:

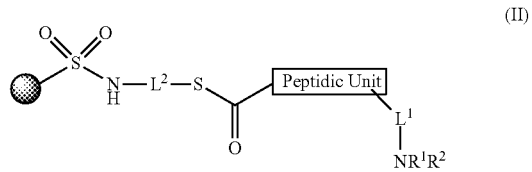

under conditions suitable to form the cyclized peptidic compound of Formula I, wherein
● is the solid-phase support;
$R^{1a}$ is selected from the group consisting of H, $NH_2$, $C_{1-8}$ alkyl, and $C_{3-8}$ cycloalkyl;
$L^1$ is selected from the group consisting of a bond, N—H, and —O—, provided that when $R^{1a}$ is $NH_2$, then $L^1$ is a bond; or provided that when $L^1$ is —O—, then $R^{1a}$ is H, $C_{1-8}$ alkyl, or $C_{3-8}$ cycloalkyl;

$R^1$ is selected from the group consisting of H, $NH_2$, $C_{1-8}$ alkyl, and $C_{3-8}$ cycloalkyl; provided than when $R^1$ is $NH_2$, then $L^1$ is a bond $R^2$ is H;

$L^2$ is selected from the group consisting of $C_{2-8}$ alkylene, $C_{3-8}$ cycloalkylene, 3- to 8-membered heterocycloalkylene, $C_{6-10}$ arylene, and 5- to 10-membered heteroarylene, each of which is optionally substituted with from 1 to 4 substituents selected from $C_{1-4}$alkyl, cyano, —C(O)$R^a$, —C(O)O$R^a$, —S$R^a$, —$C_{1-4}$alkyl—S$R^a$, and oxo, wherein the heterocycoalkylene and heteroarylene each have from 1 to 3 heteroatom ring members each independently selected from the group consisting of N, O and S; and $R^a$ is selected from the group consisting of H and $C_{1-8}$ alkyl.

In some embodiments, the method further comprises forming a transfer reaction mixture comprising the compound of Formula III:

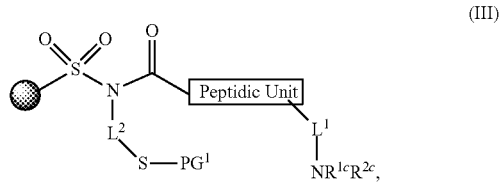

(III)

and a first acid under conditions suitable to form an intermediate of Formula IV:

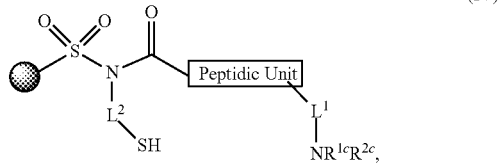

(IV)

wherein the intermediate of Formula IV undergoes an N- to S-acyl transfer reaction to form a compound of Formula IIb:

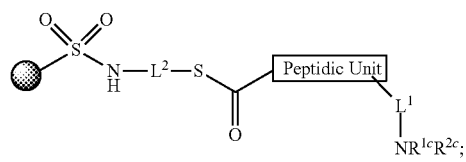

(IIb)

and forming a deprotection reaction mixture comprising the compound of Formula IIb and a second acid under conditions suitable to form the compound of Formula II

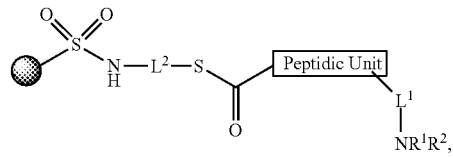

(II)

wherein $PG^1$ is a mercapto protecting group;

$R^{1c}$ is selected from the group consisting of NH-$PG^2$, H, $C_{1-8}$ alkyl, and $C_{3-8}$ cycloalkyl; provided that when $R^{1c}$ is $NH_2$, then $L^1$ is a bond; or provided that when $L^1$ is —O—, then $R^{1c}$ is H, $C_{1-8}$ alkyl, or $C_{3-8}$ cycloalkyl;

$R^{2c}$ is selected from the group consisting of $PG^2$ and H, provided that when $R^{2c}$ is H, then $R^{1c}$ is NH-$PG^2$, or provided that when $R^{2c}$ is $PG^2$, then $R^{1c}$ is H, $C_{1-8}$ alkyl, or $C_{3-8}$ cycloalkyl; and $PG^2$ is an amine protecting group; and $L^1$, $L^2$, $R^1$ and $R^2$ are as defined above.

In some embodiments, the method further comprises forming a coupling reaction mixture comprising the compound of Formula V:

(V)

and a compound of Formula VI:

(VI)

under Mitsunobu reaction conditions to form the compound of Formula III.

(III)

wherein $L^1$, $L^2$, $R^{1c}$, $R^{2c}$, $PG^1$ and $PG^2$ are as defined above.

DETAILED DESCRIPTION OF THE INVENTION

I. General

The present disclosure provides highly effective methods for preparing a diverse array of cyclized peptidic compounds. In particular, the methods of the present disclosure allows for efficiently and reliably incorporating peptoids and other N-methyl substituted amino acid derivatives into a cyclized peptidic compound using an on resin cyclative release strategy. Reliable incorporation of these groups is achieved by using a sulfonamide resin that is compatible with Fmoc solid-phase synthesis chemistry. The present disclosure provides efficient on resin cyclative release of the peptidic unit by introducing an amine labile thioester between the peptidic unit and the sulfonamide resin following peptide synthesis. Once introduced, a nucleophilic amine in the peptidic unit can cleave the thioester bond, achieving cyclization and release in a single step. Thus, the present disclosure provides methods for preparing cyclic peptidic compounds with head-to-tail linkages as well as cyclic peptidic compounds with sidechain-to-tail linkages. Overall, the described methods provide cyclized peptidic compounds in high yield and purity with improved chemical diversity using a limited number of processing steps.

II. Definitions

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), and water. Representative polar aprotic solvents include dichloromethane, chloroform, tetrahydrofuran, diethyl ether, acetone, ethyl acetate, dimethylformamide, acetonitrile and dimethyl sulfoxide. Representative non-polar solvents include alkanes (pentanes, hexanes, etc.), cycloalkanes (cyclopentane, cyclohexane, etc.), benzene, toluene, and 1,4-dioxane. Other solvents are useful in the present invention.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. The heterocycloalkyl groups can be linked via any position on the ring. For example, pyrrolidine can be 1-, 2- or 3-pyrrolidine.

"Heterocycloalkylene" refers to a heterocycloalkyl group, as defined above, linking at least two other groups. The two moieties linked to the heterocycloalkylene can be linked to the same atom or different atoms of the heterocycloalkylene.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

"Arylene" refers to an aryl group, as defined above, linking at least two other groups. The two moieties linked to the aryl can be linked to the same atom or different atoms of the aryl. Arylene groups can be substituted or unsubstituted.

"Heteroaryl" refers to a monocyclic or fused bicyclic or tricyclic aromatic ring assembly containing 5 to 12 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 5 to 6, 5 to 8, 5 to 8, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. The heteroaryl groups can be linked via any position on the ring. For example, imidazole includes 1-, 2-, 4- and 5-imidazole "Heteroarylene" refers to a heteroaryl group, as defined above, linking at least two other groups. The two moieties linked to the heteroaryl are linked to different atoms of the heteroaryl.

"Thiophilic catalyst" refers to a compound or atom that has an affinity for sulfur. Suitable thiophilic catalysts include transition metals or other compounds that have an affinity for sulfur. Typically, thiophilic catalyst of the present disclosure increase the rate of the cyclization reaction by stabilizing the sulfur and/or the transition state of the cyclization reaction. Metal thiophilic catalysts of the present disclosure include transition metals. Exemplary metal thiophilic catalyst include copper, nickel, mercury, silver, ruthenium, osmium, and strontium.

"Acid" refers to a compound that is capable of donating a proton (H+) under the Bronsted-Lowry definition. Acids useful in the present invention include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromic acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, trifluoromethanesulfonic acid, among others.

"Base" refers to a compound that is capable of accepting a proton (H+) under the Bronsted-Lowry definition. Bases include, but are not limited to, hydroxides of Group I and Group II metals such as LiOH, NaOH, KOH, RbOH, CsOH, Ca(OH)$_2$, Sr(OH)$_2$, and Ba(OH)$_2$. Bases also include amine bases such as ammonia, methylamine, trimethylamine, triethylamine, diisopropylethylamine (DIPEA), 1,8-diazabicycloundec-7-ene (DBU), 2,6-di-tert-butylpyridine, and quinuclidine.

"Non-nucleophilic base" refers to a base, as described above, that does not act as the nucleophile in substitution or trans-esterification type reactions. Typically, non-nucleophilic bases are sterically hindered by one or more bulky groups covalently linked to the basic center. The bulky groups do not block binding of a hydrogen, but do block complexation to electrophilic centers. Typical non-nucleophlic bases include, but are not limited to diisopropylethylamine (DIPEA), 1,8-diazabicycloundec-7-ene (DBU), 2,6-di-tert-butylpyridine, and phsophazene bases such as tert-Butylimino-tris(dimethylamino)phosphorene (BEMP).

"Amine non-nucleophilic base" refers to a non-nucleophilic base, as described above, where the basic center is a nitrogen atom. Typical amine non-nucleophilic bases include, but are not limited to trimethylamine, triethylamine, diisopropylethylamine (DIPEA), 1,8-diazabicycloundec-7-ene (DBU), 2,6-di-tert-butylpyridine, and quinuclidine.

"Protecting group" or "PG" refers to a moiety that is formed to render a functional moiety unreactive. The protecting group can be removed so as to restore the functional moiety to its original state. Various protecting groups and protecting reagents, including nitrogen and mercapto protecting groups, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

"Mercapto protecting group" refers to a protecting group as defined above that protects a sulfur (mercapto group). Suitable mercapto protecting groups include, but are not limited to, silyl protecting groups.

"Amine protecting group" refers to a protecting group as defined above that protects an amine groups. Suitable amine protecting groups include, but are not limited to, tertbutyoxycarbonyl (BOC), -dimethyl-3,5-dimethoxybenzyloxycarbonyl (Ddz), Monomethoxytrityl (MMT), and 4-methyltrityl (MTT).

"Natural amino acid" refers to the 22 known amino acids to occur in nature. Natural amino acids include, but are not limited to, alanine, valine, isoleucine, leucine, methionine, phenylalanine, tyrosine, tryptophan, serine, threonine, asparagine, glutamine, cysteine, selenocystine, pyrrolysine, glycine, proline, arginine, histidine, lysine, aspartic acid, and glutamic acid.

"Silyl deprotecting agent" refers to a chemical compound that accelerates the removal of a silyl protecting group by providing a fluoride ion source. Typically, silyl deprotecting agents provide a driving force for the deprotection reaction. For example, the strong bond formed by Si—F provides a driving force in the removal of silyl groups. Useful silyl deprotecting group include, but are not limited to, fluoro containing compounds such as tetra-n-butylammonium fluoride (TBAF), tris(dimethylamino)sulfonium difluorotrimethylsilicate (TASF), triethylamine trihydrofluoride (TEA-3HF), and hydrogen fluoride pyridine.

"An intermediate" refers to a compound formed in a reaction mixture that undergoes an additional transformation prior to completion of the recited step. Thus, an intermediate of the present invention is a compound that is transiently formed and consumed within a single reaction mixture.

"N- to S-acyl transfer reaction" refers to the chemical conversion of an N-acyl (amide) linkage to an S-acyl (thioester) linkage.

"Mitsunobu reaction conditions" refer to reaction conditions suitable for alkylating the nitrogen atom of the sulfonamide linked to the solid-phase support. A person of skill in the art will recognize suitable Mitsunobu reaction conditions. A Mitsunobu reaction typically includes triphenylphosphine and diisopropyl azodicarboxylate (DIAD). (*Chem. Rev.* 2009, 109(6), 2551-2651.)

"Solid-phase synthesis conditions" refers to the synthetic conditions used to prepare the linear peptide compound. Solid-phase synthesis conditions are well known in the art and include, but are not limited to, BOC and Fmoc chemistries used to incorporate amino acids or derivatives thereof into the peptidic unit. Additional solid-phase synthesis conditions include, but are not limited to, in situ incorporation of peptoid moieties as described herein.

"Peptidic unit" refers to a chemical compound with 2-10 peptidic moieties. Peptidic moieties include, but are not limited to, amino acids (D- and L-), non-natural amino acids such as depsipeptides, peptoids (N-substituted glycines), and other peptide based derivatives. Peptidic moieties also include linking peptidic moieties such a $C_{1-10}$ alkylene, where 1 to 3 carbon atoms are optionally substituted with a heteroatom selected from N, O, and S.

III. Methods for Preparing Cyclic Peptidic Compounds

Described herein are methods for preparing cyclized peptidic compounds. The approach allows for increased chemical diversity, allowing for more careful design of cyclic peptidic compounds that can, for example, have improved cell membrane permeability.

The cyclized peptidic compounds of the present disclosure can be prepared by forming a reaction mixture with a metal thiophilic catalyst, a non-nucleophilic base, and a linear peptidic compound. The linear peptidic compound is covalently linked to a solid-phase support via a linker; the linker and the linear peptidic compound are covalently linked via a thioester moiety, and the linker and solid-phase support are linked via a sulfonamide. Cyclization and cleavage of the linear peptidic compound from the solid-phase support is achieved under suitable reaction conditions described herein by cleaving the thioester moiety between the linker and the linear peptidic compound to form an amide.

In addition to the cyclization step, methods for preparing cyclized peptidic compounds of the present disclosure can further include a coupling reaction, a transfer reaction, and/or a deprotection reaction. Accordingly, in some embodiments, the present disclosure provides a method for preparing a cyclized peptidic compound of Formula Ia:

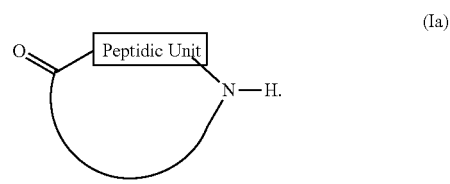

The steps include:
i) forming a coupling reaction mixture comprising a compound of Formula Va:

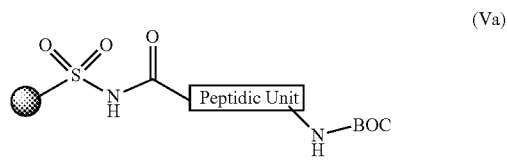

and triisopropylsilyl (TIPS)-protected mercaptoethanol under Mitsunobu reaction conditions to form a compound of Formula IIIa:

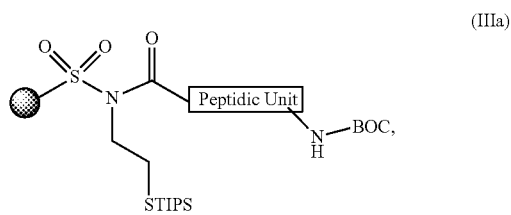

ii) forming a transfer reaction mixture comprising the compound of Formula IIIa, acetic acid, and tetra-N-butylammonium fluoride (TBAF) under conditions suitable to form an intermediate of Formula IVb:

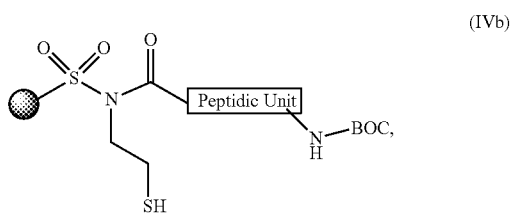

wherein the intermediate of Formula IVb undergoes an N- to S-acyl transfer reaction to form a compound of Formula IIc:

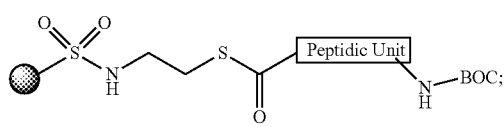

iii) forming a deprotection reaction mixture comprising the compound of Formula IIc and trifluoroacetic acid (TFA) to form a compound of Formula IIa:

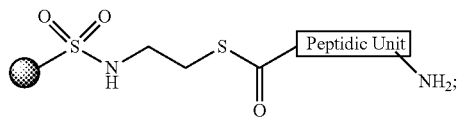

iv) forming a cyclization reaction mixture comprising silver, N,N-diisopropylethylamine (DIPEA), and the compound of Formula IIa under conditions suitable to form the cyclized peptidic compound of Formula Ia.

In the above recited steps, ● represents the solid-phase support.

Details of each conversion and the identity of the Peptidic Unit are discussed below.

A. Cyclization Reaction

Focusing first on the cyclization reaction, in some embodiments, the present disclosure provides methods for preparing a cyclized peptidic compound of Formula I:

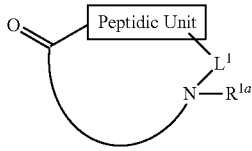

the method includes forming a reaction mixture comprising a thiophilic catalyst, a non-nucleophilic base, and a compound of Formula II:

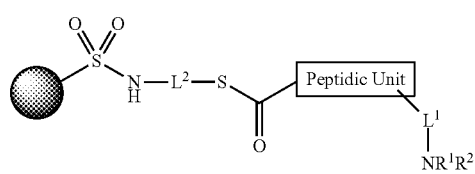

under conditions suitable to form the cyclized peptidic compound of Formula I.

Regarding Formula I, $R^{1a}$ can be H, $NH_2$, $C_{1-8}$ alkyl, or $C_{3-8}$ cycloalkyl. $L^1$ can be a bond, N—H, or —O—, provided that when $R^{1a}$ is $NH_2$, then $L^1$ is a bond; or provided that when $L^1$ is —O—, then $R^{1a}$ is H, $C_{1-8}$ alkyl, or $C_{3-8}$ cycloalkyl.

In some embodiments, $R^{1a}$ is H. In some embodiments, $L^1$ is a bond. In some embodiments, $R^{1a}$ is $NH_2$, and $L^1$ is a bond. In some embodiments, $L^1$ is —O—, and $R^{1a}$ is H or $C_{1-8}$ alkyl.

In some embodiments, the compound of Formula I has the structure of Formula Ia

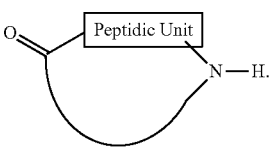

In some embodiments, the compound of Formula I has the structure of Formula Ie

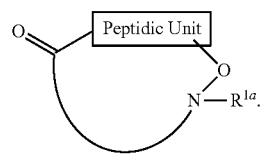

In some embodiments, the compound of Formula I has the structure of Formula If

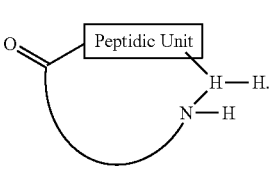

In some embodiments, the compound of Formula I has the structure of Formula Ig

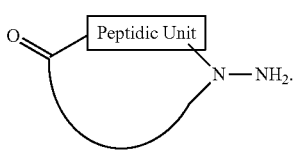

Thiophilic catalysts of the present disclosure are compounds or atoms that have an affinity for sulfur and increase the rate of the cyclization reaction. In some embodiments, the thiophilic catalysts increase the rate of the cyclization reaction by stabilizing the sulfur and/or the transition state of the cyclization reaction. The thiophilic catalysts can be a transition metal. In some embodiments, the thiophilic catalyst is a metal thiophilic catalyst. In some embodiments, the metal thiophilic catalyst is copper, nickel, mercury, silver, ruthenium, osmium, or strontium. In some embodiments, the metal thiophilic catalyst is silver.

A number of different non-nucleophilic bases can be added to the cyclization reaction mixture. Non-nucleophilic bases are well known, and it is well within the skill of an ordinary artisan to determine an appropriate non-nucleophilic base. In some embodiments, the non-nucleophilic base is an amine non-nucleophilic base. In some embodiments, the amine non-nucleophilic base is selected from the group consisting of trimethylamine, triethylamine, diisopropylethylamine (DIPEA or Hunig's Base), 1,8-diazabicycloundec-7-ene (DBU), 2,6-di-tert-butylpyridine, and quinuclidine. In some embodiments, the amine non-nucleophilic base is DIPEA.

Regarding Formula II, $R^1$ can be H, $NH_2$, $C_{1-8}$ alkyl, or $C_{3-8}$ cycloalkyl; $R^2$ can be H; and $L^1$ can be a bond, N—H, or —O—, provided that when $R^1$ is $NH_2$, then $L^1$ is a bond, or provided that when $L^1$ is —O—, then $R^1$ is H, $C_{1-8}$ alkyl, or $C_{3-8}$ cycloalkyl.

In some embodiments, $R^1$ is H. In some embodiments, $L^1$ is a bond. In some embodiments, $R^1$ is H or $C_{1-8}$ alkyl and $L^1$ is a bond. In some embodiments, $R^1$ is H or $C_{1-8}$ alkyl and $L^1$ is —O—.

In some embodiments, -$L^1$-$NR^1R^2$ of Formula II is represented by one of the following structures, where the "wavy line" indicate the point of attachment to the peptidic unit:

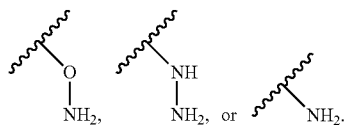

$L^2$ can be $C_{2-8}$ alkylene, $C_{3-8}$ cycloalkylene, 3- to 8-membered heterocycloalkylene, $C_{6-10}$ arylene, or 5- to 10-membered heteroarylene, each of which can be substituted with from 1 to 4 substituents selected from $C_{1-4}$alkyl, cyano, —C(O)$R^a$, —C(O)O$R^a$, —S$R^a$, —$C_{1-4}$alkyl-S$R^a$, and oxo; the heterocycoalkylene and heteroarylene each have from 1 to 3 heteroatom ring members independently selected from N, O or S; $R^a$ is H or $C_{1-8}$ alkyl. In some embodiments, $L^2$ can be $C_{2-8}$ alkylene, $C_{3-8}$ cycloalkylene, 3- to 8-membered heterocycloalkylene, or $C_{6-10}$ arylene, each of which can be substituted with from 1 to 4 substituents selected from $C_{1-4}$alkyl, cyano, —C(O)$R^a$, —C(O)O$R^a$, —S$R^a$, —$C_{1-4}$alkyl-S$R^a$, and oxo. In some embodiments, $L^2$ can be $C_{2-8}$ alkylene, $C_{3-8}$ cycloalkylene, 3- to 8-membered heterocycloalkylene, or $C_{6-10}$ arylene. In some embodiments, $L^2$ can be $C_{2-8}$ alkylene, or $C_{3-8}$ cycloalkylene. In some embodiments, $L^2$ can be $C_{2-8}$ alkylene.

In some embodiments, $L^2$ is 1,2-ethylene 1,2-propylene, 1,2-butylene, 1,2-pentylene, 1,2-hexylene, 1,3-propylene, 1,3-butylene, 1,3-pentylene, 1,3-hexylene, 1,2-cyclohexylene, 1,2-cyclopentylene, 1,3-cyclohexylene, 1,3-cyclopentylene, 2,3-tetrahydrothiopyranylene, 2,4-tetrahydrothiopyranylene, 1,2-phenylene, 1,3-phenylene, 2,3-pyridinylene, or 2,3-furanylene. In some embodiments, $L^2$ is $C_{2-8}$ alkylene. In some embodiments, $L^2$ is 1,2-ethylene 1,2-propylene, 1,2-butylene, 1,2-pentylene, 1,2-hexylene, 1,3-propylene, 1,3-butylene, 1,3-pentylene, or 1,3-hexylene. In some embodiments, $L^2$ is 1,2-ethylene.

In some embodiments, $L^2$ has the structure

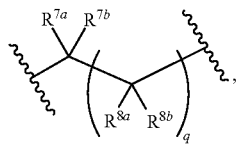

wherein, q can be an integer from 1 to 3. $R^{7a}$, $R^{7b}$ and each $R^{8a}$, and $R^{8b}$ can each be H, $C_{1-4}$ alkyl, cyano, —C(O)$R^a$, —C(O)O$R^a$, —$C_{1-4}$alkyl-S$R^a$, —S$R^a$, and oxo. Alternatively, $R^{7b}$ and $R^{8a}$ are combined with the atoms to which they are attached to form a $C_{3-8}$ cycloalkyl, $C_{6-10}$ aryl, 3- to 8-membered heterocycloalkyl, or 5- to 10-membered heteroaryl, the heterocycloalkyl and heteroaryl groups each have from 1 to 3 heteroatom ring members independently selected from N, O and S.

In some embodiments, q is 1.

In some embodiments, $R^{7a}$, $R^{7b}$ and each $R^{8a}$, and $R^{8b}$ are independently H, $C_{1-4}$alkyl, cyano, —C(O)$R^a$, —C(O)O$R^a$, —$C_{1-4}$alkyl-S$R^a$, —S$R^a$, or oxo. In some embodiments, $R^{7a}$, $R^{7b}$ and each $R^{8a}$, and $R^{8b}$ are independently H, $C_{1-4}$alkyl, or —S$R^a$. In some embodiments, at least three of $R^{7a}$, $R^{7b}$, $R^{8a}$, and $R^{8b}$ are H. In some embodiments, $R^{7a}$, $R^{7b}$ and each $R^{8a}$, and $R^{8b}$ are H.

In some embodiments, the compound of Formula II has the structure of Formula IIa:

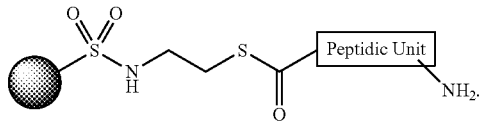

(IIa)

The cyclization reaction of the present disclosure can be performed in a variety of solvents. Suitable solvents include polar aprotic solvents such as dichloromethane, chloroform, tetrahydrofuran (THF), diethyl ether, acetone, or combinations thereof. In some embodiments, the solvent is THF.

The cyclization reaction can be conducted at various temperatures. For example, the cyclization reaction can be conducted at room temperature. In some embodiments, the cyclization reaction is conducted at a temperature of about 15-45° C. In some embodiments, the cyclization reaction is conducted at a temperature of about 20-30° C.

The cyclization reaction mixture can be at any suitable pressure. For example, the reaction mixture can be at atmospheric pressure. The reaction mixture can be also be exposed to any suitable environment, such as atmospheric gasses, or inert gasses such as nitrogen or argon.

The cyclization reaction can be conducted for any amount of time necessary to complete the cyclization reaction. Generally, the cyclization reaction is incubated for 2, 4, 6, 8, 10, 12, 18, 24, 30, 36, 42, 48, or more hours. In some embodiments, the cyclization reaction is incubated for 4-48 hours, 10-42, 12-36, or 18-30 hours. In some embodiments, the cyclization reaction is incubated for about 24 hours. In some embodiments, the cyclization reaction is performed in the absence of light. In some embodiments, the cyclization reaction is performed in the absence of light by wrapping the reaction mixture in aluminum foil.

B. Peptidic Unit

Peptidic Units of the present disclosure are linear constructs that include at least one nucleophilic amine. In the presently disclosed methods, the nucleophilic amine of the linear peptidic compound cleaves the thioester moiety linking the linear peptidic compound to a solid-phased support under suitable conditions to form a cyclized peptidic compound.

Generally, peptidic units of the present disclosure include 2 to 10 peptidic moieties. Alternatively, peptidic units of the present invention can include 2, 3, 4, 5, 6, 7, 8, 9, or 10 peptidic moieties. For example, the peptidic units of the present invention can include 2 to 10, 2 to 9, 2 to 8, 2 to 7, 2 to 6, 2 to 5, 2 to 4, or 3 to 10, 3 to 9, 3 to 8, 3 to 7, 3 to 6, 3 to 5, or 4 to 10, 4 to 9, 4 to 8, 4 to 7, 4 to 6, or 5 to 10, 5 to 9, 5 to 8, 5 to 7, or 6 to 10, 6 to 9, or 6 to 8 peptidic moieties. In some embodiments, the peptidic units can include 4 to 6 peptidic moieties. In some embodiments, the peptidic unit can include 6 peptidic moieties.

The peptidic units of the present invention can have a molecular weight of from about 150 to about 3000 Daltons. Other molecular weights for the peptidic units of the present invention include about 250 to about 3000 Daltons, or about 250 to about 2500 Daltons, or about 250 to about 2000 Daltons, or about 250 to about 1500 Daltons, or about 250 to about 1000 Daltons, or about 500 to about 3000 Daltons, or about 750 to about 3000 Daltons, or about 1000 to about 3000 Daltons, or about 500 to about 2000 Daltons, or about 500 to about 1500 Daltons, or about 500 to about 1000 Daltons. One of skill in the art appreciates that other molecular weights for the peptidic units of the present invention are also useful depending on the nature of the peptidic moieties.

Peptidic moieties include, but are not limited to, amino acids (D- and L-), non-natural amino acids such as depsipeptides, peptoids (N-substituted glycines), beta-amino acids, gamma-amino acids, homo-amino acids, N-methyl amino acids, and appropriate combinations thereof (e.g. homo-depsipeptide, N-methyl homo-amino acid), and other peptide based derivatives. The non-natural amino acids of the present disclosure also include variations in the side chain beyond the 22 natural amino acids. For example, in some embodiments, the non-natural amino acids include side chains with one or more optionally substituted aryl or heteroaryl rings which are often useful pharmacophores. Peptidic moieties also include linking groups, such as $C_{1-4}$ alkylene.

Amino acid moieties have a general structure as shown below

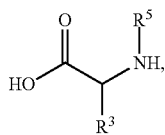

where $R^3$ is the side-chain of the amino acid moiety and is defined below. $R^5$ is H or $C_{1-8}$ alkyl. When $R^5$ is methyl, the structure shown above is an N-methyl amino acid.

Beta amino acid moieties have a general structure as shown below

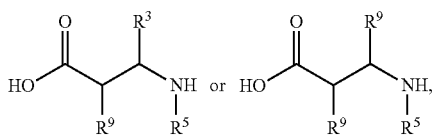

where $R^3$ is the side-chain of the beta amino acid moiety and is defined below. $R^5$ is H or $C_{1-8}$ alkyl. When $R^5$ is methyl, the structure shown above is an N-methyl beta amino acid. $R^9$ is H, $C_{1-8}$ alkyl, or OH.

Gamma amino acid moieties have a general structure as shown below

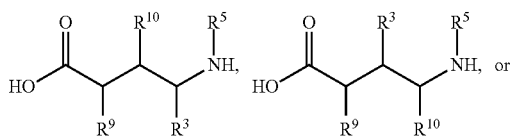

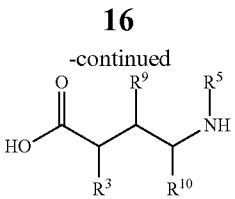

where $R^3$ is the side-chain of the gamma amino acid moiety and is defined below. $R^5$ is H or $C_{1-8}$ alkyl. When $R^5$ is methyl, the structure shown above is an N-methyl gamma amino acid. $R^9$ and $R^{10}$ are each independently H, $C_{1-8}$ alkyl, or OH.

Depsipeptide moieties have a general structure as shown below

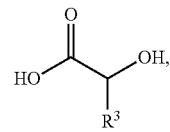

where $R^3$ is the side-chain of the depsipeptide moiety and is defined below. A beta depsipeptide moiety includes an additional methylene between the COOH and C—$R^3$ groups or the C—$R^3$ and OH groups.

Peptoid moieties have a general structure as shown below,

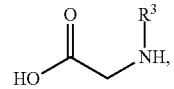

where $R^3$ is the side-chain of the peptoid moiety and is defined below.

From the above defined structures it is clear that various combinations and modifications of peptidic moieties within the peptidic unit are possible. For example, in some embodiments, the methylene added by the beta derivatives described above can be further substituted with an $R^3$, $R^5$, $R^9$ or $R^{10}$ group. Further, it is understood that in addition to the beta derivatives described above, alkylene groups larger than methylene, such as $C_{1-6}$ or $C_{1-4}$ alkylene can be incorporated into the peptidic moieties described herein.

Peptidic moieties of the present disclosure also include linking moieties such as $C_{1-10}$ alkylene, where 1 to 3 carbon atoms are optionally substituted with a heteroatom selected from N, O, and S. In some embodiments, a linking peptidic moiety is

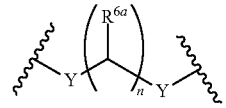

wherein each Y is independently $NR^5$, C(O), O, or S; $R^5$ is H or $C_{1-8}$ alkyl; each $R^{6a}$ is H or halogen; and n is an integer from 0 to 8.

The nucleophilic amine of the peptidic unit can be any suitable amine. Suitable amines include a terminal amine and a non-terminal amine. A terminal amine is an amine that is the final atom in the main-chain of a linear peptidic unit. A non-terminal amine is an amine that is not part of the main-chain of the peptidic unit (i.e., the non-terminal amine is part of a side-chain attached to the backbone linear peptidic unit). In some embodiments, the nucleophilic amine is a terminal amine (head-to-tail cyclization). In some embodiments, the nucleophilic amine is a non-terminal amine (sidechain-to-tail cyclization). In some embodiments the nucleophilic amine is an amine functional group (—NHR$^1$), the amine of an aminooxy functional group (—O—NH$_2$), or either amine of a hydrazine functional group (—NH—NH$_2$), where R$^1$ is as defined above in subsection A.

General limiting factors regarding the suitable nucleophilic amine includes the size of ring formed in the cyclization reaction. Referring to the sidechain-to-tail cyclization discussed above, an exemplary suitable nucleophilic amine includes the amine of a lysine residue. In some embodiments, the lysine is the third, fourth, fifth or sixth amino acid of the peptidic unit (counting from the point of attachment to the solid-phased support), and readily undergoes cyclization under suitable conditions.

In some embodiments, the peptidic unit is defined by the composition of the peptidic moieties, X, incorporated therein:

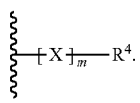

wherein, m is an integer from 2 to 10;
each X is independently, C$_{3-8}$ cycloalkylene, X$^1$—C$_{3-8}$ cycloalkylene, heterocycloalkylene, X$^1$-heterocycloalkylene, C$_{6-10}$ arylene, —X$^1$—C$_{6-10}$ tharylene, heteroarylene, —X$^1$-heteroarylene,

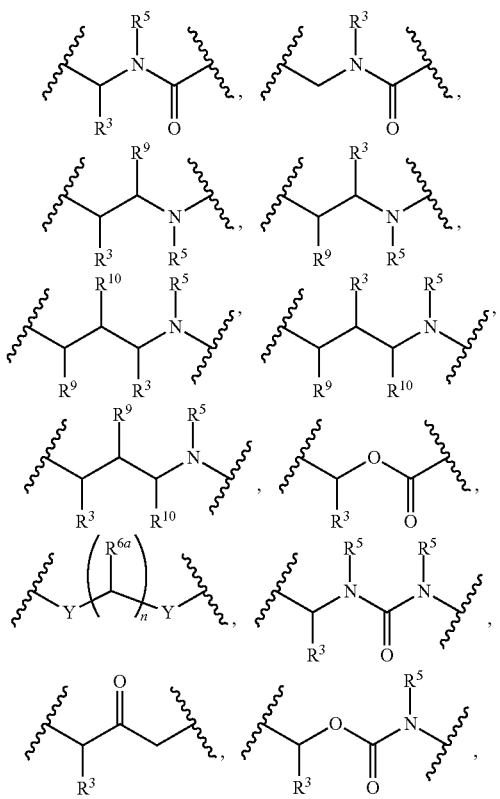

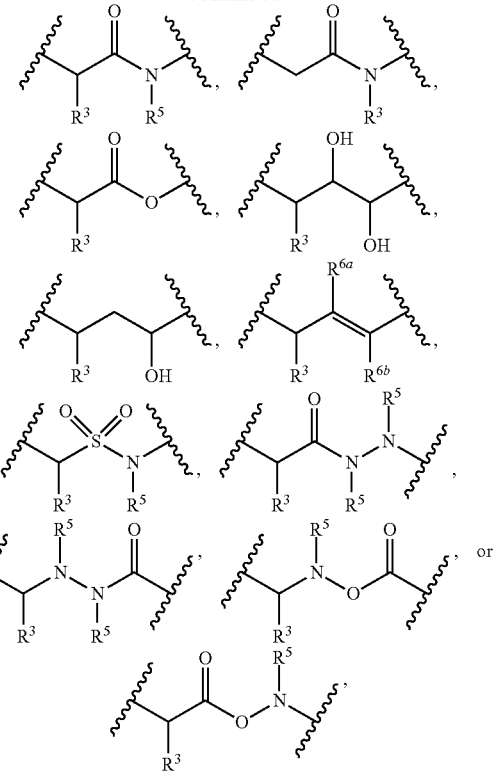

wherein each heterocycoalkylene includes from 3 to 8 ring members having 1 to 3 heteroatom ring members, each independently selected from N, O and S, and each heteroarylene includes from 5 to 10 ring members having 1 to 3 heteroatom ring members, each independently selected from the group consisting of N, O and S.

Each Y is independently a bond, CH$_2$, NR$^5$, O, S, S(O), or S(O)$_2$.

Each n is an integer from 1 to 8.

Each R$^3$ is H, halogen, cyano, C$_{1-8}$ alkyl, C$_{2-8}$ alkenyl, C$_{2-8}$ alkynyl, C$_{1-8}$ haloalkyl, —OR$^d$, —X$^1$—OR$^d$, —SR$^b$, —X$^1$—SR$^b$, —NR$^b$R$^d$, —X$^1$—NR$^b$R$^d$, C(O)R$^b$, —X$^1$—C(O)R$^b$, —C(O)OR$^b$, —X$^1$—C(O)OR$^b$, —C(O)NR$^b$R$^c$, —X$^1$—C(O)NR$^b$R$^c$, —OC(O)NR$^b$R$^c$, —X$^1$—OC(O)NR$^b$R$^c$, —NR$^b$C(O)R$^c$, —X$^1$—NR$^b$C(O)R$^c$, —NR$^b$C(O)$_2$R$^c$, —X$^1$—NR$^b$C(O)$_2$R$^c$, —NR$^b$C(O)NR$^b$R$^c$, —X$^1$—NR$^b$C(O)NR$^b$R$^c$, —S(O)$_2$NR$^b$R$^c$, —X$^1$—S(O)$_2$NR$^a$R$^b$, —NR$^b$C(NH)NR$^b$R$^c$, —X$^1$—NR$^b$C(NH)NR$^b$R$^c$, C$_{3-8}$ cycloalkyl, X$^1$—C$_{3-8}$ cycloalkyl, C$_{6-10}$ aryl, —X$^1$—C$_{6-10}$aryl, heterocycloalkyl, —X$^1$-heterocycloalkyl, heteroaryl, and —X$^1$-heteroaryl. The C$_{3-8}$ cycloalkyl, C$_{6-10}$ aryl, heterocycloalkyl, and heteroaryl moieties of R$^3$ are optionally substituted with 1 to 4 substituents each independently selected from the group consisting of C$_{1-4}$ alkyl, halogen, cyano, —OR$^b$, —X$^1$—OR$^b$, —SR$^b$, —X$^1$—SR$^b$, —NR$^b$R$^d$, and —X$^1$—NR$^b$R$^d$. Each heterocycloalkyl includes from 3 to 8 ring members having 1 to 3 heteroatom ring members, each independently selected from N, O and S. Each heteroaryl includes 5 to 10 ring members having 1 to 3 heteroatom ring members, each independently selected from N, O and S.

R$^4$ is H, C$_{1-8}$ alkyl, —OR$^d$, —NR$^b$R$^d$, —[C(H)(R$^3$)]$_{1-6}$—NR$^b$R$^d$, —X$^1$—C(O)R$^b$, —C(O)R$^b$, —NH—C(O)R$^b$, C(O) OR$^b$, —X$^1$—C(O)OR$^b$, —C(O)NR$^b$R$^c$, or C$_{3-8}$ cycloalkyl.

Each R$^5$ is independently H or C$_{1-8}$ alkyl; alternatively, R$^3$ and R$^5$ within the same X unit are combined with the atoms to which they are attached to form 5- to 6-membered heterocycloalkyl ring having from 1 to 3 additional heteroatoms each independently selected from the group consisting of N, O and S. In some embodiments, the 5- to 6-membered heterocycloalkyl ring formed by combining $R^3$ and $R^5$ is optionally further substituted with from 1 to 3 substituents selected from halogen, cyano, $C_{1-8}$ alkyl, $C_{2-8}$ alkenyl, $C_{2-8}$ alkynyl, $C_{1-8}$ haloalkyl, —$OR^b$, —$X^1$—$OR^b$, —$SR^b$, —$X^1$—$SR^b$, —$NR^bR^d$, —$X^1$—$NR^bR^d$, $C(O)R^b$, —$X^1$—$C(O)R^b$, —$C(O)OR^b$, —$X^1$—$C(O)OR^b$, —$C(O)NR^bR^c$, —$X^1$—$C(O)NR^bR^c$, —$NR^bC(O)R^c$, —$X^1$—$NR^bC(O)R^c$, —$NR^bC(O)_2R^c$, —$X^1$—$NR^bC(O)_2R^c$, —$S(O)_2NR^bR^c$, or —$X^1$—$S(O)_2NR^aR^b$.

Each $R^{6a}$ and $R^{6b}$ are each independently H, $C_{1-4}$ alkyl or halogen.

Each $X^1$ is independently $C_{1-6}$ alkylene.

$R^9$ and $R^{10}$ are each independently H, $C_{1-8}$ alkyl, or OH.

Each $R^b$ and $R^c$ is independently H, $C_{1-8}$ alkyl, or $C_{1-8}$ haloalkyl.

Each $R^d$ is independently H, $C_{1-8}$alkyl, $C_{1-8}$ haloalkyl, or $NH_2$.

In some embodiments, each X can independently be $C_{3-8}$ cycloalkylene, $X^1$—$C_{3-8}$ cycloalkylene, heterocycloalkylene, $X^1$-heterocycloalkylene, $C_{6-10}$ arylene, —$X^1$—$C_{6-10}$arylene, heteroarylene, —$X^1$-heteroarylene,

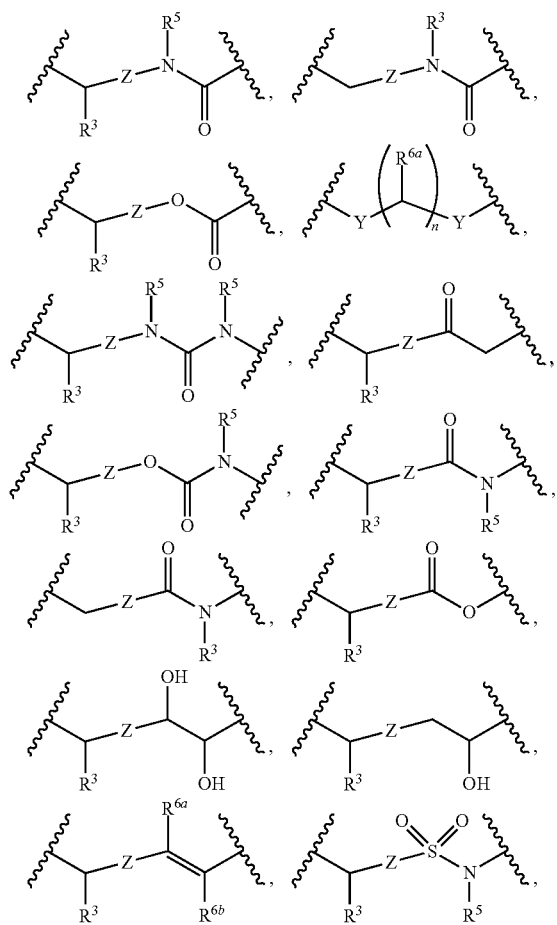
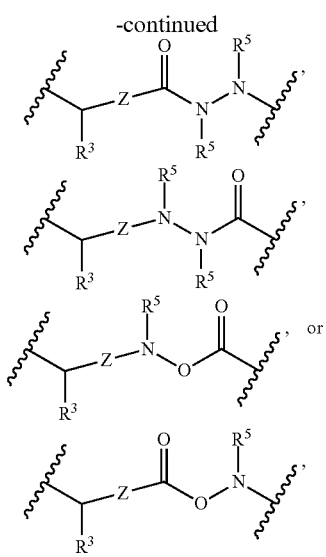

wherein each Z is a bond or can independently be $C_{1-6}$ alkylene, —$[C(H)(R^3)]_{1-6}$—, $C_{3-8}$ cycloalkylene, $X^1$—$C_{3-8}$ cycloalkylene, heterocycloalkylene, $X^1$-heterocycloalkylene, $C_{6-10}$ arylene, —$X^1$—$C_{6-10}$arylene, heteroarylene, or —$X^1$-heteroarylene, wherein each heterocycoalkylene includes from 3 to 8 ring members having 1 to 3 heteroatom ring members, each independently selected from N, O and S, and each heteroarylene includes from 5 to 10 ring members having 1 to 3 heteroatom ring members each independently selected from the group consisting of N, O and S, and wherein each $X^1$ is independently $C_{1-6}$ alkylene.

In some embodiments, m is an integer from 2 to 6. In some embodiments, m is an integer from 2 to 9, 2 to 8, 2 to 7, 2 to 6, 2 to 5, 2 to 4 or 2 to 3. In some embodiments, m is 2, 3, 4, 5, 6, 7, 8, 9, or 10. In some embodiments, m is 6.

In some embodiments, each $R^3$ can be an amino acid side chain. For example, $R^3$ can be the side chain of alanine, valine, isoleucine, leucine, methionine, phenylalanine, tyrosine, tryptophan, serine, threonine, asparagine, glutamine, cysteine, selenocystine, pyrrolysine, glycine, proline, arginine, histidine, lysine, aspartic acid, or glutamic acid. In some embodiments, each $R^3$ can be hydrogen, $C_{1-6}$ alkyl, $C_{1-6}$ alkylene-S—$C_{1-6}$ alkyl, phenyl, 4-hydroxyphenyl, $C_{1-6}$ hydroxyalkyl, $C_{1-6}$ alkyl-SH, $C_{1-6}$ alkyl-$NH_2$, $C_{1-6}$ alkyl-C(O)$NH_2$, $C_{1-6}$ alkyl-NHC(=$NH_2^+$)$NH_2$, $C_{1-6}$ alkyl-C(O)OH, $C_{1-6}$ alkyl-indol-3-yl, $C_{1-6}$ alkyl-imidazol-4-yl, or can be combined with $R^5$ and the atoms to which they are attached to form pyrrolidine. In some embodiments, each $R^3$ can be hydrogen, methyl, isopropyl, isobutyl, sec-butyl, —$CH_2CH_2$—S—$CH_3$, phenyl, 4-hydroxyphenyl, hydroxymethyl, 1-hydroxyethyl, mercaptomethyl, 4-aminobut-1-yl, —$CH_2$—$C(O)NH_2$, —$CH_2CH_2$—$C(O)NH_2$, —$(CH_2)_3$—NHC(=$NH_2^+$)$NH_2$, —$CH_2$—$C(O)OH$, —$CH_2CH_2$—$C(O)OH$, —$CH_2$-indol-3-yl, —$CH_2$-imidazol-4-yl, or can be combined with $R^5$ and the atoms to which they are attached to form pyrrolidine.

In some embodiments, $R^4$ is H, $C_{1-8}$ alkyl, —$OR^d$, —$NR^bR^d$, —$[C(H)(R^3)]_{1-6}$—$NR^bR^d$, $C(O)R^b$, —NH—C(O)$R^b$ or $C_{3-8}$ cycloalkyl. In some embodiments, $R^4$ is H, $C_{1-4}$ alkyl, N—C(O)—$CH_3$, —C(O)—$CH_3$, —$NH_2$, —NH—$NH_2$, or —$ONH_2$. In some embodiments, $R^4$ is H, $C_{1-4}$ alkyl, —$C(H)(R^3)NHR^5$, N—C(O)—$CH_3$, —C(O)—$CH_3$, —$NH_2$, —NH—$NH_2$, or —$ONH_2$. In some embodiments, $R^4$ is —$NH_2$, —NH—$NH_2$, or —$ONH_2$. In some embodiments, $R^4$ is —$NH_2$. In some embodiments, $R^4$ is —C(H)($R^3$)$NR^bR^d$. In some embodiments, $R^4$ is —C(H)($R^3$)$NHR^5$.

In some embodiments, $R^5$ can be H or $C_{1-8}$ alkyl. In some embodiments, $R^5$ can be combined with $R^3$ of the same peptidic moiety to form a pyrrolidine. In some embodiments, $R^5$ can be H or methyl. In some embodiments, $R^5$ can be H. In some embodiments, $R^5$ can be methyl.

In some embodiments, each X is independently:

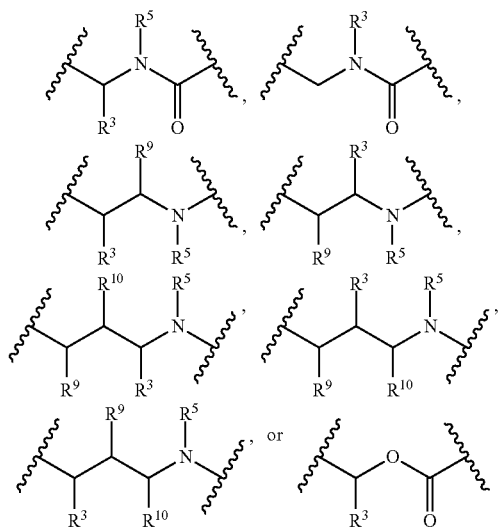

where $R^3$, $R^5$, $R^9$ and $R^{10}$ are as defined above.

In some embodiments, each X is independently:

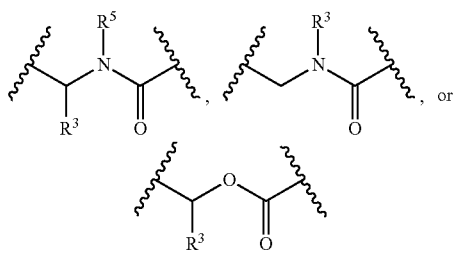

where $R^3$ and $R^5$ are as defined above.

In some embodiments, the peptidic unit includes at least one natural amino acid. In some embodiments, the peptidic unit includes all natural amino acids. In some embodiments, the peptidic unit includes at least one peptoid moiety. In some embodiments, the peptidic unit includes at least one N-methylated amino acid.

In some embodiments, the peptidic unit has the formula shown below:

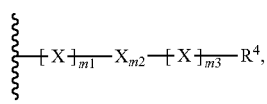

where $R^4$ and X are as defined above. The subscripts m1 and m3 are each independently an integer from 0 to 9 provided that the sum of m1 and m3 does not exceed 9, and the subscript m2 is 1. Thus, it can be seen that $X_{m1}$—$X_{m2}$—$X_{m3}$ represents a subformula of $X_m$.

In some embodiments, the compound of Formula I is represented by the compound of Formula Ii or Formula Ij

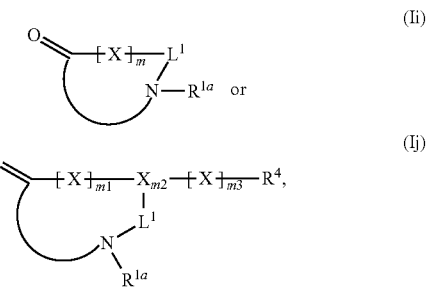

where X, m, $L^1$, $R^4$, and $R^{1a}$ are as defined above. $L^1$ in Formula Ii is attached to the terminal peptidic moiety (X) (e.g., when m is 2 the sequence is —$X_1$—$X_2$-$L^1$-; when m is 4 the sequence is —$X_1$—$X_2$—$X_3$—$X_4$-$L^1$-). Referring to Formula Ij, subscripts m1 and m3 are each independently an integer from 0 to 9 provided that the sum of m1 and m3 does not exceed 9, and the subscript m2 is 1.

In some embodiments, the peptidic unit is defined by the composition of the peptidic moieties, X, and has the following formula:

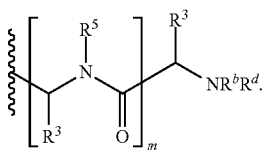

In some embodiments, the peptidic unit is defined by the composition of the peptidic moieties, X, and has the following formula:

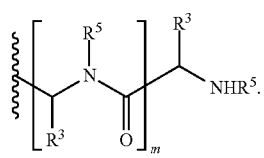

In some embodiments, the compound of Formula I has the following structure:

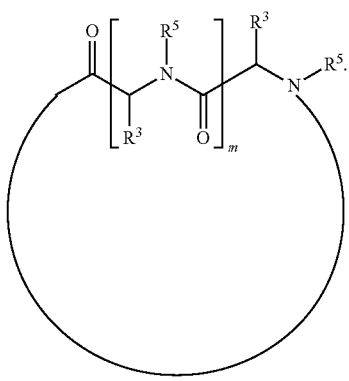

In some embodiments, the compound of Formula II has the following structure:

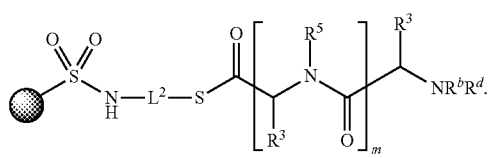

In some embodiments, the compound of Formula II has the following structure:

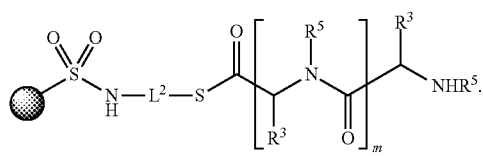

In some embodiments, the compound of Formula II has the following structure:

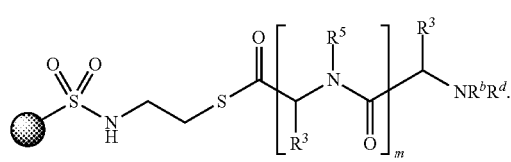

In some embodiments, the compound of Formula II has the following structure:

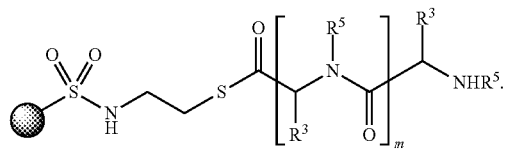

Methods of solid-phase peptide synthesis for preparing the peptidic units described herein are known in the art. Further considerations of peptidic unit synthesis are discussed in sub-section D, below.

It is understood that the above formulas for the peptidic unit described in this section can include one or more protecting groups, if necessary, during one or more steps of the synthetic methods described herein. A person of skill in the art can readily determine when a protecting group is necessary, and can choose from the many known protecting groups in the art, such as those disclosed in *Protective Groups in Organic Synthesis*, 4th edition, T. W. Greene and P. G. M. Wuts, John Wiley & Sons, New York, 2006, which is incorporated herein by reference in its entirety. Exemplary protecting group include nitrogen, mercapto, and hydroxyl protecting groups.

C. Transfer Reaction & Deprotection Reaction

The transfer reaction and deprotection reaction is carried out after peptide synthesis is complete. In some embodiments, the present method includes a transfer and deprotection reaction. The transfer reaction provides conditions suitable for an N to S acyl transfer reaction to occur following removal of the protecting group from the mercapto moiety of Formula III, shown below. This reaction introduces an amine labile thioester bond that allows for the on-resin cyclization reaction to occur. The deprotection reaction removes $PG^2$ from the compound of Formula IIb, shown below.

The transfer reaction can be carried out by forming a transfer reaction mixture comprising a compound of Formula III:

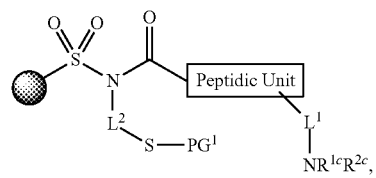

and a first acid under conditions suitable to form an intermediate of Formula IV:

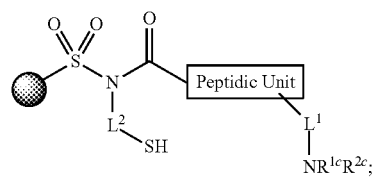

the conditions are also sufficient for the intermediate of Formula IV to undergo an N- to S-acyl transfer reaction to form a compound of Formula IIb:

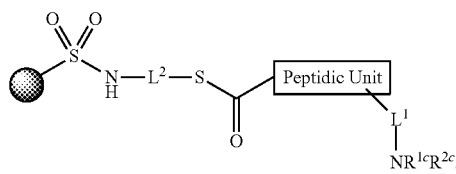

Referring to Formula III, $PG^1$ is a mercapto protecting group. In some embodiments, $PG^1$ is a silyl protecting group. In some embodiments, the silyl protecting group is trimethylsilyl (TMS), trietherylsilyl (TES), tert-butyldimethylsilyl (TBS), tert-butyldiphenylsilyl (TBDPS), and triisopropylsilyl (TIPS). In some embodiments, the silyl protecting group is TIPS.

$R^{1c}$ can be $NH-PG^2$, H, $C_{1-8}$ alkyl, or $C_{3-8}$ cycloalkyl; $L^1$ can be a bond, N—H, or —O—, provided that when $R^{1c}$ is $NH-PG^2$, then $L^1$ is a bond; or provided that when $L^1$ is —O—, then $R^{1c}$ is H, $C_{1-8}$ alkyl, or $C_{3-8}$ cycloalkyl; $R^{2c}$ can be $PG^2$ or H, provided that when $R^{2c}$ is H, then $R^{1c}$ is $NH-PG^2$, or provided that when $R^{2c}$ is $PG^2$, then $R^{1c}$ is H, $C_{1-8}$ alkyl, or $C_{3-8}$ cycloalkyl. In some embodiments, $R^{1c}$ is $NH-PG^2$, $R^{2c}$ is H, and L is a bond. In some embodiments, $R^{1c}$ is H or $C_{1-8}$ alkyl, $R^{2c}$ is $PG^2$, and $L^1$ is —O—. In some embodiments, $R^{1c}$ is H or $C_{1-8}$ alkyl, $R^{2c}$ is $PG^2$, and $L^1$ is a bond.

$PG^2$ is an amine protecting group. In some embodiments, the amine protecting group is tertbutyoxycarbonyl (BOC), -dimethyl-3,5-dimethoxybenzyloxycarbonyl (Ddz), Monomethoxytrityl (MMT), or 4-methyltrityl (MTT). In some embodiments, PG² is BOC. In some embodiments, PG² is -dimethyl-3,5-dimethoxybenzyloxycarbonyl (Ddz), Monomethoxytrityl (MMT), or 4-methyltrityl (MTT). In some embodiments, PG² is MMT.

L² can be as defined above for Formula II in sub-section A.

L¹, R¹ᶜ, and R¹ᶜ are as defined above for Formulas IV and IIb.

In some embodiments, the transfer reaction further comprises a silyl deprotecting agent. Silyl deprotecting agents are chemical compounds that accelerate the removal of a silyl protecting group. In some embodiments, the silyl deprotecting agent allows for selective deprotecting of PG¹ without the removal of PG². Silyl deprotecting agents are well known in the art and are generally fluoro containing compounds. In some embodiments, the silyl deprotecting agent is tetra-n-butylammonium fluoride (TBAF), tris(dimethylamino)sulfonium difluorotrimethylsilicate (TASF), triethylamine trihydrofluoride (TEA-3HF), or hydrogen fluoride pyridine. In some embodiments, the silyl deprotecting agent is tetra-n-butylammonium fluoride (TBAF).

The first acid used in the transfer reaction can be an alkanoic acid, carboxylic acid, mineral acid, a sulfonic acid or similar type acid. In some embodiments, the first acid is hydrochloride, hydrogenbromide, hydrogeniodide, hydrogenfluoride, acetic acid, trifluoro acetic acid or combinations thereof. In some embodiments, the first acid is acetic acid.

As in the cyclization reaction described above, the transfer reaction can be performed in a variety of solvents. Suitable solvents include polar aprotic solvents such as dichloromethane, chloroform, tetrahydrofuran (THF), diethyl ether, acetone or combinations thereof. In some embodiments, the solvent is THF. In some embodiments, the solvent is dichloromethane. In some embodiments, the solvent is a combination of THF and dichloromethane.

In some embodiments, the transfer reaction mixture has a pH of from 1 to 5. In some embodiments, the transfer reaction mixture has a pH of from 2 to 4. In some embodiments, the transfer reaction mixture has a pH of about 3.

The transfer reaction can be conducted at various temperatures. For example, the transfer reaction can be conducted at room temperature. In some embodiments, the transfer reaction is conducted at a temperature of about 15-45° C. In some embodiments, the transfer reaction is conducted at a temperature of about 20-30° C.

The transfer reaction mixture can be at any suitable pressure. For example, the reaction mixture can be at atmospheric pressure. The reaction mixture can be also be exposed to any suitable environment, such as atmospheric gasses, or inert gasses such as nitrogen or argon.

The transfer reaction can be conducted for any amount of time necessary to complete the transfer reaction. Generally, the transfer reaction is incubated for 0.25 0.5 0.75, 1, 1.25, 1.5, 1.75, 2, 2.25, 2.5, 2.75, 3, 3.5, 4, 4.5, 5, 6, 7, or more hours. In some embodiments, the transfer reaction is incubated for 0.5-4, 0.75-3, or 1-2 hours. In some embodiments, the transfer reaction is incubated for about 1.5 hours.

The deprotection reaction can be carried out by forming a deprotection reaction mixture comprising the compound of Formula IIb

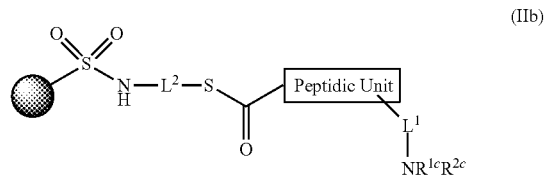

and a second acid under conditions suitable to form the compound of Formula II,

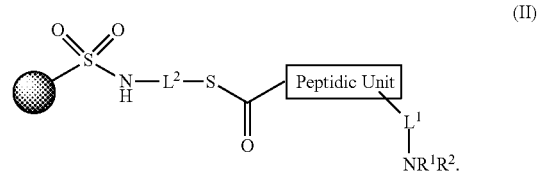

L², L¹, R¹ᶜ, R²ᶜ, R¹, and R² can be as defined above.

The second acid used in the deprotection reaction can be an alkanoic acid, carboxylic acid, mineral acid, a sulfonic acid or similar type acid. In some embodiments, the second acid is hydrochloride, hydrogenbromide, hydrogeniodide, hydrogenfluoride, acetic acid, trifluoro acetic acid, trichloroacetic acid or combinations thereof. In some embodiments, the second acid is hydrochloride, hydrogenbromide, hydrogeniodide, hydrogenfluoride, acetic acid, trifluoro acetic acid or combinations thereof. In some embodiments, the second acid is trifluoro acetic acid. In some embodiments, the second acid is trichloro acetic acid.

The deprotection reaction can be performed in a variety of solvents. Suitable solvents include polar aprotic solvents such as dichloromethane, chloroform, tetrahydrofuran (THF), diethyl ether, acetone or combinations thereof. In some embodiments, the solvent is dichloromethane. In some embodiments, the solvent is THF. In some embodiments, the solvent is a combination of THF and dichloromethane.

In some embodiments, the deprotection reaction mixture has a pH of less than 3. In some embodiments, the deprotection reaction mixture has a pH less than 2. In some embodiments, the deprotection reaction mixture has a pH of less than 1.

The deprotection reaction can be conducted at various temperatures. For example, the deprotection reaction can be conducted at room temperature. In some embodiments, the deprotection reaction is conducted at a temperature of about 15-45° C. In some embodiments, the deprotection reaction is conducted at a temperature of about 20-30° C.

The deprotection reaction mixture can be at any suitable pressure. For example, the reaction mixture can be at atmospheric pressure. The reaction mixture can be also be exposed to any suitable environment, such as atmospheric gasses, or inert gasses such as nitrogen or argon.

The deprotection reaction can be conducted for any amount of time necessary to complete the deprotection reaction. Generally, the deprotection reaction is incubated for 0.25 0.5 0.75, 1, 1.25, 1.5, 1.75, 2, 2.25, 2.5, 2.75, 3, 3.5, 4, 4.5, 5, 6, 7, or more hours. In some embodiments, the deprotection reaction is incubated for 0.5-4, 0.5-2, or 0.75-1.25 hours. In some embodiments, the deprotection reaction is incubated for 1 hour. In some embodiments, the deprotection reaction is incubated for about 1.5 hours.

As described above, the transfer reaction and the deprotection reaction can be performed in two separate reaction mixtures. In some embodiments, the transfer and deprotection reaction are performed in a single reaction mixture. The combined transfer and deprotection reaction removes both PG$^1$ and PG$^2$ in a single reaction mixture. The combined transfer and deprotection also provides conditions suitable for an N to S acyl transfer reaction to occur after PG$^1$ is removed.

Accordingly, in some embodiments, the transfer and deprotection reaction can be carried out by forming a transfer/deprotection reaction mixture comprising the compound of Formula III:

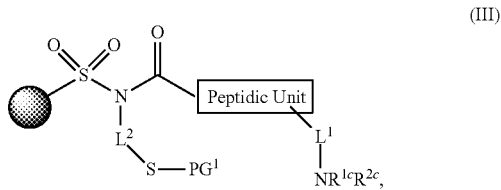

(III)

and an acid under conditions suitable to form an intermediate of Formula IVa:

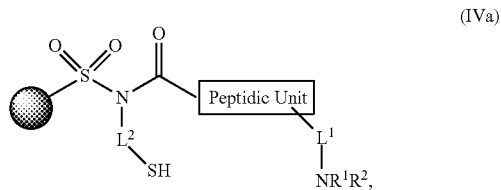

(IVa)

the conditions are also sufficient for the intermediate of Formula IVa to undergo an N- to S-acyl transfer reaction to form a compound of Formula II:

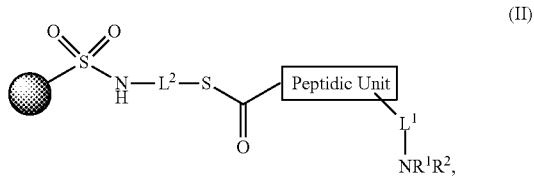

(II)

R$^{1c}$, R$^{1c}$, R$^1$, R$^2$, L$^1$, L$^2$, PG$^1$, and PG$^2$ are as described above.

In some embodiments, the transfer/deprotection reaction further comprises a silyl deprotecting agent as described in the transfer reaction above.

It is understood that additional intermediates are formed during the transfer/deprotection reaction. For example, PG$^1$ can be removed and N- to S-acyl transfer can occur prior to PG$^2$ removal. However, to maximize clarity, the only intermediate identified is the group where both PG$^1$ and PG$^2$ are removed (Formula IVa). As defined in sub-section C, PG$^2$ is an amine protecting group and is a found in R$^{1c}$ or R$^{2c}$ in Formula III, above.

The acid used in the transfer/deprotection reaction can be an alkanoic acid, carboxylic acid, mineral acid, a sulfonic acid or similar type acid. In some embodiments, the acid is hydrochloride, hydrogenbromide, hydrogeniodide, hydrogenfluoride, acetic acid, trifluoro acetic acid or combinations thereof. In some embodiments, the acid is trifluoro acetic acid.

The transfer/deprotection reaction can be performed in a variety of solvents. Suitable solvents include polar aprotic solvents such as dichloromethane, chloroform, tetrahydrofuran (THF), diethyl ether, acetone or combinations thereof. In some embodiments, the solvent is dichloromethane. In some embodiments, the solvent is THF. In some embodiments, the solvent is a combination of THF and dichloromethane.

In some embodiments, the transfer/deprotection reaction mixture has a pH of less than 3. In some embodiments, the transfer/deprotection reaction mixture has a pH less than 2. In some embodiments, the transfer/deprotection reaction mixture has a pH of less than 1.

In some embodiments, the pH of the reaction mixture is increased by addition of a non-nucleophilic base after a sufficient amount of time. A sufficient amount of time is any time necessary to remove the PG$^1$ and PG$^2$ groups; however, complete removal of both groups is not necessary before addition of a non-nucleophilic base. Generally, a sufficient amount of time includes 20 minutes, 30 minutes, 45 minutes, 1 hour, 1.25 hours, 1.5 hours, 2 hours, 3 hours or more. In some embodiments, a sufficient amount of time is 30 minutes. In some embodiments, a sufficient amount of time is 1 hour. In some embodiments, a sufficient amount of time is 1.5 hours.

In some embodiments, the pH of the transfer/deprotection reaction solution after addition of a non-nucleophilic base is from 1 to 5. In some embodiments, the transfer reaction mixture has a pH of from 2 to 4. In some embodiments, the transfer reaction mixture has a pH of about 3.

A variety of non-nucleophilic bases are useful in adjusting the pH of the transfer/deprotection reaction mixture. Non-nucleophilic bases are well known, and it is well within the skill of an ordinary artisan to determine an appropriate non-nucleophilic base. In some embodiments, the non-nucleophilic base is an amine non-nucleophilic base. In some embodiments, the amine non-nucleophilic base is selected from the group consisting of trimethylamine, triethylamine, diisopropylethylamine (DIPEA or Hunig's Base), 1,8-diazabicycloundec-7-ene (DBU), 2,6-di-tert-butylpyridine, and quinuclidine. In some embodiments, the amine non-nucleophilic base is DIPEA.

The transfer/deprotection reaction can be conducted at various temperatures. For example, the transfer/deprotection reaction can be conducted at room temperature. In some embodiments, the transfer/deprotection reaction is conducted at a temperature of about 15-45° C. In some embodiments, the transfer/deprotection reaction is conducted at a temperature of about 20-30° C.

The transfer/deprotection reaction mixture can be at any suitable pressure. For example, the reaction mixture can be at atmospheric pressure. The reaction mixture can be also be exposed to any suitable environment, such as atmospheric gasses, or inert gasses such as nitrogen or argon.

The transfer/deprotection reaction can be conducted for any amount of time necessary to complete the transfer reaction. Generally, the transfer/deprotection reaction is incubated for 0.25 0.5 0.75, 1, 1.25, 1.5, 1.75, 2, 2.25, 2.5, 2.75, 3, 3.5, 4, 4.5, 5, 6, 7, or more hours. In some embodiments, the transfer/deprotection reaction is incubated for 0.5-4, 0.75-3, or 1-2 hours. In some embodiments, the transfer/deprotection reaction is incubated for about 1.5 hours. In some embodiments, the transfer/deprotection reaction is incubated for about 1 hour.

D. Coupling Reaction

The coupling reaction adds a protected mercapto group to the nitrogen atom of the sulfonamide linked to the solid-phase support. The mercapto group introduced in this step provides the thioester linkage necessary for the cyclization reaction in downstream steps of the process. Therefore, in some embodiments, the present method also includes a coupling reaction. The coupling reaction includes contacting a protected mercapto-alkyl-alcohol (defined in Formula VI) with the compound of Formula (V) under Mitsunobu reaction conditions.

The coupling reaction can be carried out by forming a coupling reaction mixture comprising a compound of Formula V:

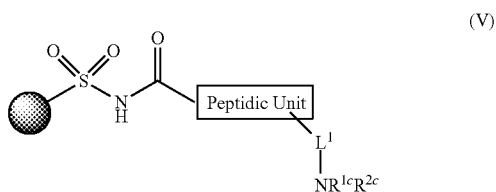

and a compound of Formula VI:

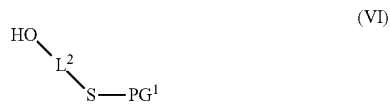

under Mitsunobu reaction conditions to form the compound of Formula III:

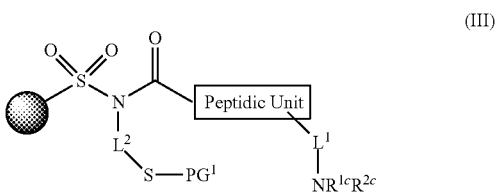

$R^{1c}$, $R^{1c}$, $L^1$, $L^2$, $PG^1$, and $PG^2$ are as described above.

In some embodiments, the compound of Formula VI is mercaptoethanol, 3-mercaptopropan-1-ol, 2,3-dimercaptopropan-1-ol, 4-mercaptopropan-1-ol, and 2-mercaptopropan-1-ol, 2-mercaptocyclohexan-1-ol, 2-mercaptocyclopentan-1-ol, 2-mercaptophenol, 3-mercaptopyridin-2-ol, or 3-mercaptofuran-2-ol, wherein each mercapto group is protected with the protecting group $PG^1$. In some embodiments, the compound of Formula VI is mercaptoethanol, 3-mercaptopropan-1-ol, 2,3-dimercaptopropan-1-ol, 4-mercaptopropan-1-ol, or 2-mercaptopropan-1-ol, wherein each mercapto group is protected with the protecting group $PG^1$. In some embodiments, the compound of Formula VI is mercaptoethanol, wherein the mercapto group is protected with the protecting group $PG^1$.

The coupling reaction can also include triphenylphosphine, a solvent, and an azodicarboxylate. The azodicarboxylate can include, but not limited to, diethyl azodicarboxylated or diisopropyl azodicarboxylated. In some embodiments the Mitsunobu reaction conditions include an inert atmosphere with a suitable inert gas such as nitrogen, argon, neon and combinations thereof. In some embodiments, the inert gas is nitrogen. The solvent can include any suitable solvent including tetrahydrofuran, dimethylformamide, dichloromethane, and combinations thereof. In some embodiments, the solvent is tetrahydrofuran combined with dichloromethane.

The coupling reaction can be conducted at various temperatures. For example, the coupling reaction can be conducted at room temperature. In some embodiments, the coupling reaction is conducted at a temperature of about 15-45° C. In some embodiments, the coupling reaction is conducted at a temperature of about 20-30° C.

The coupling reaction mixture can be at any suitable pressure. For example, the reaction mixture can be at atmospheric pressure. The reaction mixture can be also be exposed to any suitable environment, such as atmospheric gasses, or inert gasses such as nitrogen or argon.

The coupling reaction can be conducted for any amount of time necessary to complete the coupling reaction. Generally, the coupling reaction is incubated for 2, 4, 6, 8, 10, 12, 15, 18, 21, 24, 30, 36, 42, 48, or more hours. In some embodiments, the coupling reaction is incubated for 4-48 hours, 10-42, 12-36, 12-24, or 15-21 hours. In some embodiments, the coupling reaction is incubated for about 18 hours.

Typically, the coupling reaction is carried out after the solid phase synthesis of the peptidic unit is complete (i.e. after the final peptidic moiety is added to the peptidic unit). As described in sub-section B, above, the peptidic moieties of the peptidic unit can include, but are not limited to, amino acid moieties and amino acid surrogates such as depsipeptides and peptoids. In embodiments where the main-chain of the peptidic unit includes a terminal amine, said amine includes an acid labile protecting group. In some embodiments, the acid labile protecting group of the terminal amine is BOC.

It is understood that any primary and secondary amines present in the peptidic unit will include a protecting group prior to the Mitsunobu reaction. In some embodiments, the protecting group is an acid labile amine protecting group. In some embodiments, the acid labile protecting group is selected from the group consisting of tertbutyoxycarbonyl (BOC), -dimethyl-3,5-dimethoxybenzyloxycarbonyl (Ddz), Monomethoxytrityl (MMT), and 4-methyltrityl (MTT).

A person of skill in the art will recognize that when two or more amines are present in the peptidic unit, orthogonal deprotection of the "cyclization amine" (i.e. the amine that acts as a nucleophile to form the cyclized peptidic compound) is desirable. Accordingly, in embodiments where two or more amines are present in the peptidic unit, the cyclization amine is orthogonally protected. Orthogonal protection allows for selective de-protection of the cyclization amine. As a non-limiting example of orthogonal protection, the cyclization amine is protected with -dimethyl-3,5-dimethoxybenzyloxycarbonyl (Ddz), Monomethoxytrityl (MMT), or 4-methyltrityl (MTT), and all other amines are protected with tertbutyoxycarbonyl (BOC). MMT, MTT, and DDZ can be removed using 2% TFA. Comparatively, BOC is removed in 30% TFA. The selective deprotection of the cyclization amine ensures that the desired cyclized peptidic compound is formed.

E. Solid-Phase Synthesis of Peptidic Unit

In some embodiments, the methods of the present invention further comprise solid-phase synthesis of the peptidic unit. In such embodiments, the compound of Formula V

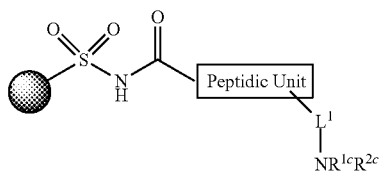

(V)

is prepared by sequential addition of peptidic moieties under solid-phase synthesis conditions to the compound of Formula VII:

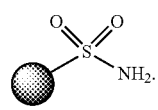

(VII)

It is understood that the sphere of Formula VII (●) is a solid-phase support with an attached sulfonamide functional group. A variety of solid-phase supports known in the art are useful in the present invention. Useful solid-phase supports include, resins made of polystyrene, polyacrylate, polyacrylamide, and combinations thereof. It is well established that linking groups such as $C_{1-6}$ alkyl provide sufficient separation between the resin and the sulfonamide for efficient loading and subsequent synthesis reactions.

A variety of methods for preparing sulfonamide resins are known in the art. As a non-limiting example, sulfonamide resins of the present disclosure can be prepared by contacting a resin comprising a terminal amine with 4-sulfamoylbutanoic acid under conditions shown below:

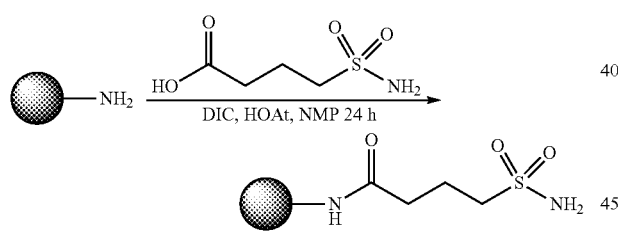

DIC: N,N'-diisoproplcarbodiimide, a carboxyl activating agent; HOAt: 1-hydroxy-7-azabenotriazole, a carboxyl activating agent; NMP: N-methyl-2-pyrrolidone, a polar aprotic solvent.

As described in the paragraphs above, the compound produced in the preceding reaction is a compound of Formula VII.

As with methods of preparing sulfonamide resins, method of preparing amino acid loaded resins (i.e. addition of the first peptidic moiety) are known in the art. As a non-limiting Example, an Fmoc loaded sulfonamide resin can be prepared as follows:

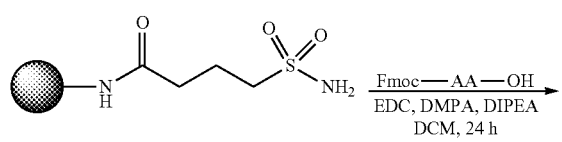

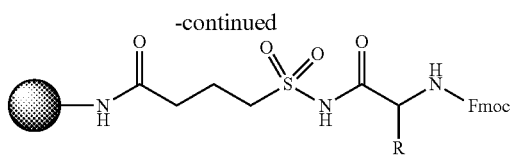

EDC: 1-Ethyl-3-(3-dimethylaminopropyl)carbodiimide, a carboxyl activating agent; DMAP: 4-Dimethylaminopyridine, a non-nucleophilic base; DIPEA: N,N-diisopropylethylamine, a non-nucleophilic base; DCM: dichloromethane, a solvent.

Standard solid phase synthesis techniques are used to sequentially add peptidic moieties to the compound of Formula VII. As described in sub-section B, above, peptidic units of the present disclosure include 2-10 peptidic moieties, X. Peptidic moieties of the peptidic unit form to make peptides, depsipeptides, peptoids, and other peptidic derivatives. Advantageously, the sulfonamide solid-phase support provides compatible chemistry for solid phase synthesis techniques incorporating a peptoid moiety into the peptidic unit. As a non-limiting example, a peptoid moiety can be added to a peptidic unit using the following in situ conversions, where "A," "B," and "C" represent peptidic moieties already incorporated into the peptidic unit:

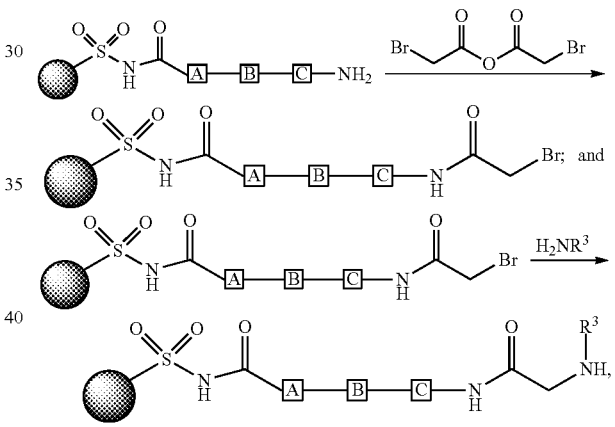

wherein $R^3$ is as defined above in sub-section B.

When incorporating peptidic moieties that have cross-reactive functional groups (i.e. an amino acid (one carboxylic acid group and an amine group)), protecting groups are added to prevent undesirable polymerization reactions. Protecting groups useful in the sequential addition of peptidic moieties under solid-phase synthesis conditions of the present disclosure include both tertbutyoxycarbonyl (BOC) and fluorenylmethyloxycarbonyl chloride (Fmoc). Thus, the solid phase synthesis techniques useful in the present invention include both BOC and Fmoc chemistries. Accordingly, a further example of incorporating a peptoid moiety into the peptidic unit includes the following chemical conversion. Again, "A," "B," and "C" represent peptidic moieties already incorporated into the peptidic unit:

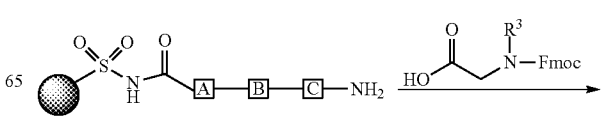

-continued

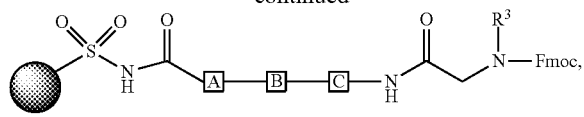

wherein R³ is as defined above in sub-section B. The next peptidic moiety in the reaction scheme above is added after Fmoc removal. Advantageously, the use of Fmoc chemistry during solid-phase synthesis of the peptidic unit allows for easy incorporation of N-alkyl and peptoid moieties into the peptidic unit. When N-alkyl or peptoid moieties are incorporated into a peptidic unit using BOC chemistry, the necessary acidic deprotection step produces an undesirable side reaction to acid-sensitive residues including an N-alkyl bond or N—R³ bond. The use of Fmoc chemistry during linear peptide synthesis mitigates this issue by limiting the total number of acid deprotection steps necessary when preparing cyclized peptides of the present disclosure. Accordingly, the methods of the present disclosure provide increased chemical diversity available for cyclized peptidic compounds.

The final peptidic moiety is incorporated into the peptidic unit may have a primary or secondary amine. In embodiments where the final peptidic moiety incorporated includes an amine, said amine is protecting group with an acid labile protecting group. As discussed above, the peptidic unit can include from 2-10 peptidic moieties. Thus, the final peptidic moiety can be the $2^{nd}$, $3^{rd}$, $4^{th}$, $5^{th}$, $6^{th}$, $7^{th}$, $8^{th}$, $9^{th}$, or $10^{th}$ peptidic moiety added, depending on the desired length of the peptidic unit. In some embodiments, the acid labile protecting group of the final peptidic moiety is tertbutyoxycarbonyl (BOC), -dimethyl-3,5-dimethoxybenzyloxycarbonyl (Ddz), Monomethoxytrityl (MMT), or 4-methyltrityl (MTT).

Further solid-phase synthesis methods making linear peptidic compounds with the amino acid derivatives described herein are known in the art.

F. Particular Embodiments of the Disclosure

In some embodiments, the compound of Formula I is represented by the compound of Formula Ib

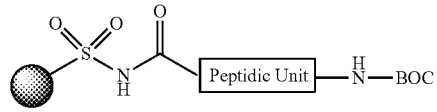
(Ib)

and is prepared by:
i) forming a coupling reaction mixture comprising a compound of Formula Vb:

(Vb)

and triisopropylsilyl (TIPS)-protected mercaptoethanol under Mitsunobu reaction conditions to form a compound of Formula IIIb:

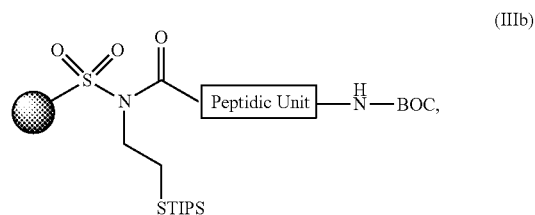
(IIIb)

ii) forming a transfer reaction mixture comprising the compound of Formula IIIb, acetic acid, and tetra-N-butylammonium fluoride (TBAF) under conditions suitable to form an intermediate of Formula IVc:

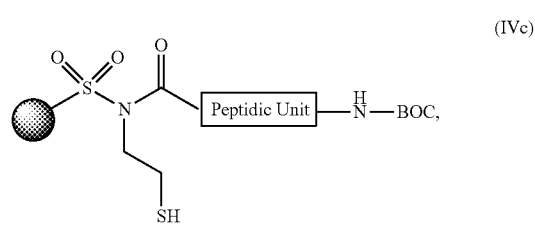
(IVc)

wherein the intermediate of Formula IVc undergoes an N- to S-acyl transfer reaction to form a compound of Formula IId:

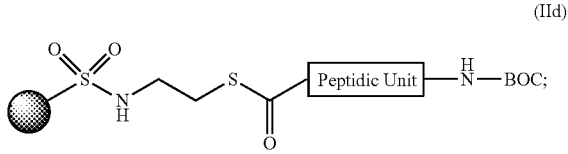
(IId)

iii) forming a deprotection reaction mixture comprising the compound of Formula IId and trifluoroacetic acid (TFA) to form a compound of Formula IIe:

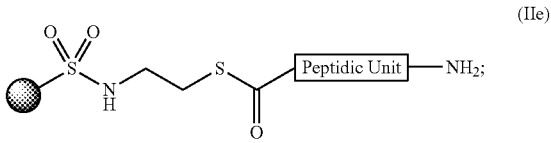
(IIe)

iv) forming a cyclization reaction mixture comprising silver, N,N-diisopropylethylamine (DIPEA), and the compound of Formula IIe under conditions suitable to form the cyclized peptidic compound of Formula Ia.

In some embodiments, the compound of Formula Ic

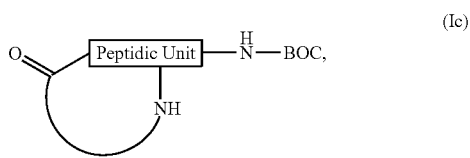

is prepared by:

i) forming a coupling reaction mixture comprising a compound of Formula Vc:

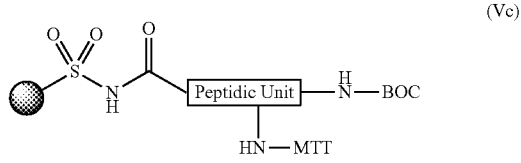

and triisopropylsilyl (TIPS)-protected mercaptoethanol under Mitsunobu reaction conditions to form a compound of Formula IIIc:

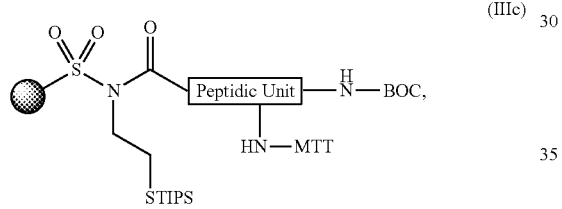

ii) forming a transfer reaction mixture comprising the compound of Formula IIIc, acetic acid, and tetra-N-butylammonium fluoride (TBAF) under conditions suitable to form an intermediate of Formula IVd:

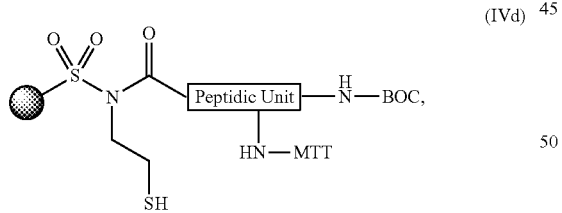

wherein the intermediate of Formula IVd undergoes an N- to S-acyl transfer reaction to form a compound of Formula IIf:

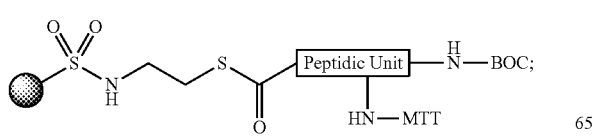

iii) forming a deprotection reaction mixture comprising the compound of Formula IIf and trifluoroacetic acid (TFA) to form a compound of Formula IIg:

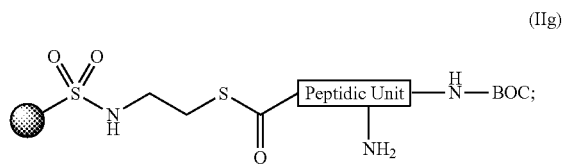

iv) forming a cyclization reaction mixture comprising silver, N,N-diisopropylethylamine (DIPEA), and the compound of Formula IIg under conditions suitable to form the cyclized peptidic compound of Formula Ic.

In some embodiments, the MTT protecting group is replaced with an MMT protecting group.

In some embodiments, the transfer reaction and deprotection reaction of steps ii) and iii) in the above method of preparing a cyclized peptide are performed in a single reaction mixture using a single acid.

In some embodiments, the above described method further comprises i) forming a second deprotection reaction mixture comprising the compound of Formula Ic and trifluoroacetic acid (TFA) to form a compound of Formula Id:

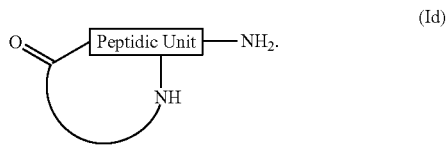

In some embodiments, the compound of Formula Ih

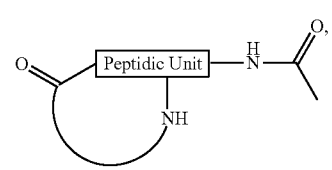

is prepared by:

i) forming a coupling reaction mixture comprising a compound of Formula Vd:

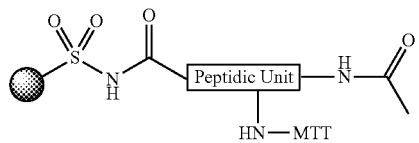

and triisopropylsilyl (TIPS)-protected mercaptoethanol under Mitsunobu reaction conditions to form a compound of Formula IIId:

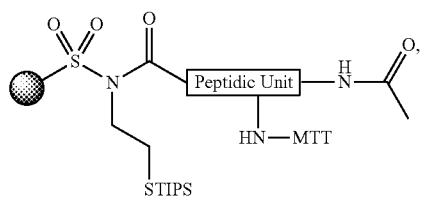

ii) forming a transfer reaction mixture comprising the compound of Formula IIId, acetic acid, and tetra-N-butylammonium fluoride (TBAF) under conditions suitable to form an intermediate of Formula IVd:

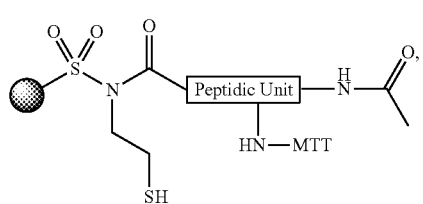

wherein the intermediate of Formula IVe undergoes an N- to S-acyl transfer reaction to form a compound of Formula IIh:

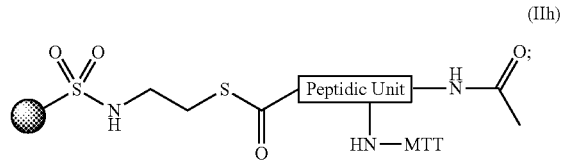

iii) forming a deprotection reaction mixture comprising the compound of Formula IIh and trifluoroacetic acid (TFA) to form a compound of Formula IIi:

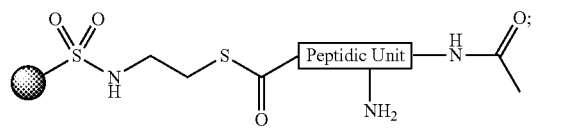

iv) forming a cyclization reaction mixture comprising silver, N,N-diisopropylethylamine (DIPEA), and the compound of Formula IIi under conditions suitable to form the cyclized peptidic compound of Formula Ih.

In some embodiments, the MTT protecting group is replaced with an MMT protecting group.

In some embodiments, the transfer reaction and deprotection reaction of steps ii) and iii) in the above method of preparing a cyclized peptide are performed in a single reaction mixture using a single acid.

IV. EXAMPLES

Example 1: Linear Peptide Synthesis

Linear peptide synthesis of the peptidic unit was achieved using standard florenylmethyloxycarbonyl (Fmoc) solid phase peptide synthesis protocols on a 4-sulfamylbutyryl-loaded support. The final amino acid in the linear synthesis (position 1, using standard N→C nomenclature) used an acid-labile tert-butoxycarbonyl (BOC) protecting group instead of an Fmoc protection group.

Example 2: Linear Peptide Synthesis with In Situ Incorporation of Peptoid Moieties Linear peptide synthesis was performed as described in Example 1. At positions where a peptoid moiety is desired, Fmoc chemistry, as described above, or in situ incorporation were employed. The reaction diagrams and conditions used for in situ incorporation as provided below.

First, the deprotected N-terminus of the peptidic unit was reacted with 2-bromoacetic anhydride and DIPEA in NMP:

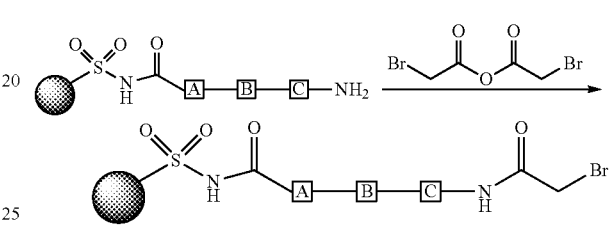

The bromoacetamide-terminated resin was then treated with primary amine and DIPEA in NMP to yield the N-terminal peptoid:

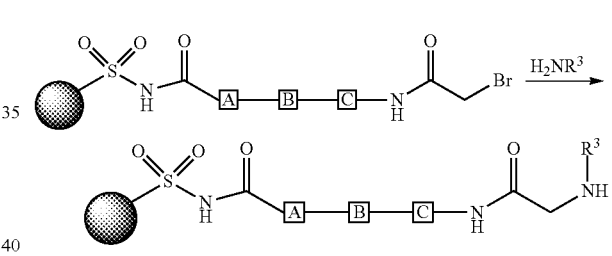

In the diagrams above, peptidic moieties already incorporated into the peptidic unit are represented by "A," "B," and "C."

Example 3: Alkylation of Acyl Sulfonamide Linker (Activation of Safety-Catch Linker)

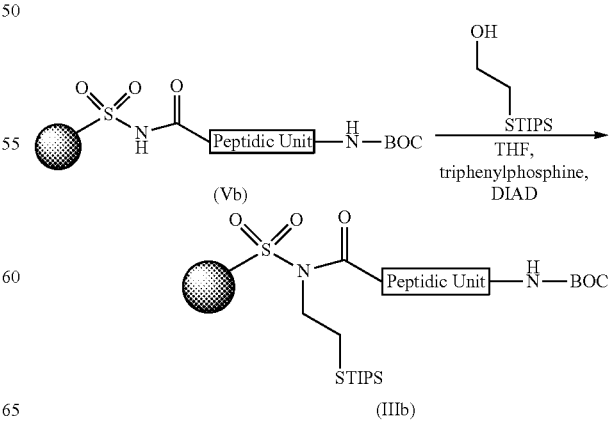

After the peptidic unit is synthesized (shown generically as Formula Vb), the resin with the N-terminal BOC protected linear peptide (10 umol) was washed with dichloromethane (DCM) and swelled in dry tetrahydrofuran (THF). A solution of triisopropylsilyl (TIPS)-protected mercaptoethanol (20 equiv, 0.5-1.0 M) and triphenylphosphine (20 equiv) in THF was added to the resin, followed by the addition of diisopropyl azodicarboxylate (DIAD) (20 equiv). The reaction mixture was shaken for 18 hours to produce a compound of Formula IIIb. The resin was then washed with DCM (3×), THF (3×), DCM (3×).

Example 4: Deprotection of TIPS-Protected Thiol and N→S Acyl Transfer

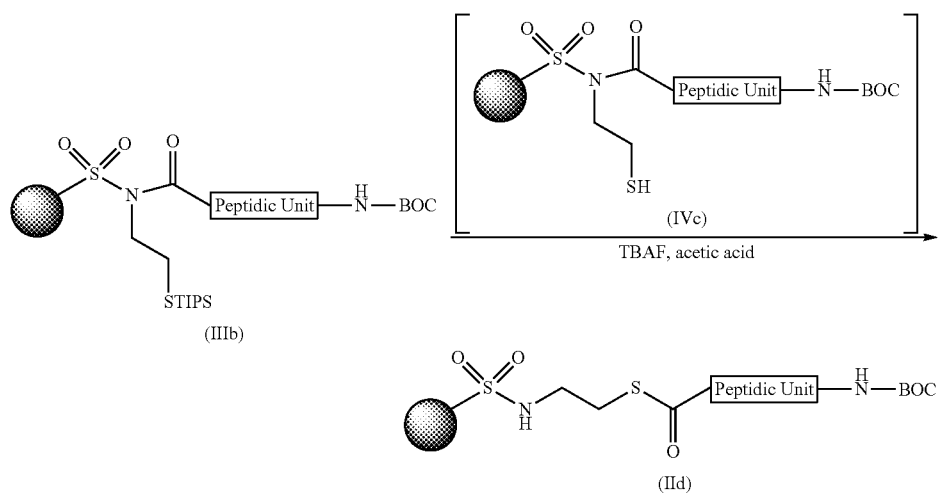

After alkylation, the resin loaded with a compound of Formula IIIb was swelled in dry THF. A solution of tetra-N-butylammonium fluoride (TBAF) (0.1 M) and glacial acetic acid (0.2 M) in dry THF (pH=3) was added to the resin and the reaction mixture was shaken for 1.5 hours. The reaction produces an intermediate of Formula IVc, which then undergoes an N→S acyl transfer to provide a Compound of Formula IId. The resin was then washed with DCM (3×), THF (3×), DCM (3×).

Example 5: Deprotection of N-Terminal BOC

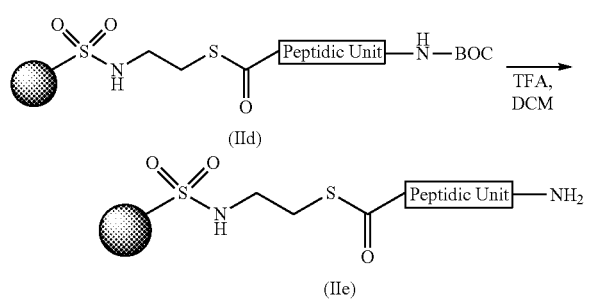

After the transfer reaction of Example 4, the resin with a compound of Formula IId was swelled in dry DCM. A solution of 30% trifluoroacetic acid (TFA) in DCM was added to the resin. The reaction mixture was shaken for 1 hour to provide a compound of Formula IIe. The resin was then washed with DCM (3×), THF (3×), DCM (3×).

Example 6: Cyclative Release

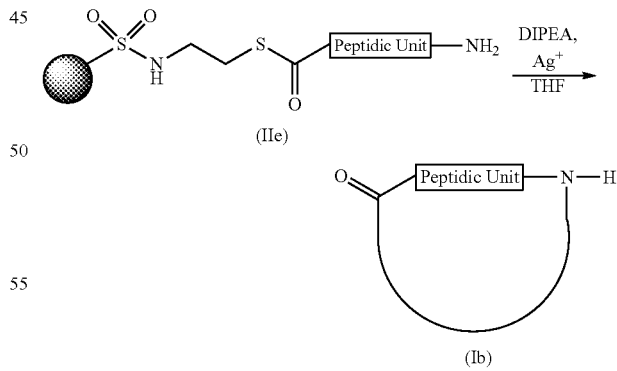

The resin was rinsed with dry unstabilized THF. A solution of silver trifluoroacetate (cat., 1 equiv, 5 mM) and N,N-diisopropylethylamine (DIPEA) (3 equiv) in dry unstabilized THF was added to the resin. The reaction mixture was shaken for 24 hours in a glass vial wrapped in aluminum foil. Cyclative release separates the peptidic unit from the solid phase via cleavage of the thioester bond.

Example 7: Simultaneous Deprotection of TIPS-Protected Thiol, N→S Acyl Transfer, and Deprotection of N-Terminal BOC

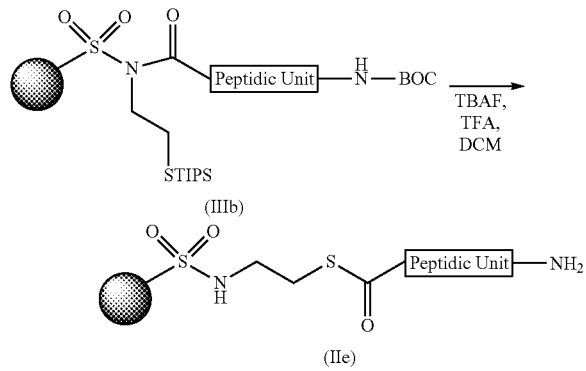

After alkylation, the resin loaded with a compound of Formula IIIb was swelled in dry DCM. A solution of tetra-N-butylammonium fluoride (TBAF) (0.1 M) and 30% TFA in dry DCM was added to the resin and the reaction mixture was shaken for 1.5 hours. This conversion simultaneously removes the TIPS and BOC protecting groups. The deprotected thiol group undergoes an N→S acyl transfer to provide a Compound of Formula IIe.

Example 8: Simultaneous Deprotection of TIPS-Protected Thiol, N→S Acyl Transfer, and Deprotection of N-Terminal BOC

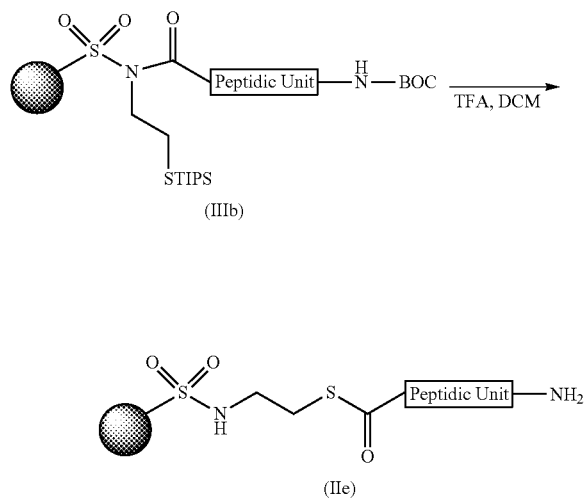

After alkylation, the resin loaded with a compound of Formula IIIb was swelled in dry DCM. A solution of 30% TFA in dry DCM was added to the resin and the reaction mixture was shaken for 1.5 hours. This conversion simultaneously removes the TIPS and BOC protecting groups. The deprotected thiol group undergoes an N→S acyl transfer to provide a Compound of Formula IIe.

Examples 4 and 5, 7, and 8 provide different deprotection and N→S acyl transfer strategies and/or conditions to provide a compound of Formula IIe can then be used in a cyclative release reaction as described in Example 6. To quantitate the efficiency of the various deprotection and N→S acyl transfer strategies, the cyclative release reaction of Example 6 is performed. Following cyclative release, remaining peptidic units ("linear product") is cleaved from the resin with 20 equivalents of propyl amine. The product recovered during propyl amine cleavage is referred to as linear product because it is the amount of product recovered that did not cyclize in the cyclative release reaction. The amount of product recovered in each reaction was determined by integrating the peak area of the expected m/z cyclative release product and the peak area of the expected m/z linear product by LCMS UV (214 nm). Cyclative release efficiency was calculated by dividing the cyclative release peak area by the sum of cyclative release peak area and the linear peak area (i.e., cyclative release peak area/(cyclative release peak area+linear peak area).

When the sequence of the peptidic unit is Resin-Leu-Tyr-Pro-(D-Ala)-Leu-Ala-Boc, the cyclative release efficiency for each strategy is shown below in Table 1.

TABLE 1

| Cyclative Release Efficiency | |
|---|---|
| Deprotection Strategy | Cyclative Release Efficiency (%)* |
| Stepwise (Examples 4 and 5) | 78 |
| Simultaneous (Example 7) | 4 |
| Simultaneous (Example 8) | 4 |

Example 9: Cyclative Release Using Silver

Peptidic units with 6 amino acids were synthesized as described in Example 1. After synthesis of the peptidic unit, Seq 1, 2, 5, and 6 underwent alkylation and deprotection steps as described in Examples 3-5. Seq 3, 4, 7, and 8 underwent an alkylation and deprotections as described in Examples 3-5, except that benzyl alcohol (BnOH) was used instead of mercaptoethanol. Cyclative release, as described in Example 6, was performed on all Seq in the presence of silver (+) and in the absence of silver (−). Following cyclative release, remaining peptidic units ("linear product") were cleaved from the resin with 20 equivalents of propyl amine. The product recovered during propyl amine cleavage is referred to as linear product because it is the amount of product recovered that did not cyclize in the cyclative release reaction. The amount of product recovered in each reaction was determined by integrating the peak area of the expected m/z cyclative release product and the peak area of the expected m/z linear product by LCMS UV (214 nm). Cyclative release efficiency was calculated by dividing the cyclative release peak area by the sum of cyclative release peak area and the linear peak area (i.e., cyclative release peak area/(cyclative release peak area+linear peak area).

The results are shown below in Table 2. The data demonstrates that the N→S acyl transfer reaction that forms the thioester and a thiophilic catalyst are necessary for efficient cyclative release.

TABLE 2

Cyclative Release Efficiency

| | | | | | | Conditions | | |
|---|---|---|---|---|---|---|---|---|
| | | Sequence (Position N→C) | | | | Sulfonamide Alkyl group | Cyclative release Cyclization efficiency Silver | (%) |
| Seq | 1 | 2 | 3 | 4 | 5 | 6 | | |
| 1 | Ala | Leu | D-Ala | Pro | Tyr | Leu | TIPS-mercapto-ethanol | + | 83 |
| 2 | Ala | Leu | D-Ala | Pro | Tyr | Leu | TIPS-mercapto-ethanol | − | 4 |
| 3 | Ala | Leu | D-Ala | Pro | Tyr | Leu | Benzyl alcohol | + | 0 |
| 4 | Ala | Leu | D-Ala | Pro | Tyr | Leu | Benzyl alcohol | − | 1 |
| 5 | Ala | Leu | D-Ala | Pro | Tyr | Phe | TIPS-mercapto-ethanol | + | 72 |
| 6 | Ala | Leu | D-Ala | Pro | Tyr | Phe | TIPS-mercapto-ethanol | − | 9 |
| 7 | Ala | Leu | D-Ala | Pro | Tyr | Phe | Benzyl alcohol | + | 5 |
| 8 | Ala | Leu | D-Ala | Pro | Tyr | Phe | Benzyl alcohol | − | 7 |

Example 10: Cyclative Release and the Length of the Peptidic Unit

Peptidic units of varying length (5-9 amino acids) were synthesized as described in Example 1. After synthesis of the peptidic unit, the alkylation, deprotection, and cyclative release steps as described in Examples 3-6 were performed, except that the cyclization reaction was incubated for 40 hours instead of 24. After the cyclative release reaction, remaining peptidic units ("linear product") were cleaved from the resin with 20 equivalents of propyl amine. Cyclative release efficiency was calculated as described in Example 9 only for sequences 10 (54%) and 11 (54%). The "Cyclative Release" amount reported in Table 3 is the integrated peak area of the 214 nm UV signal in the LCMS trace that corresponds to the expected m/z cyclative release product. The cyclative release reaction conditions used are those described in Example 6.

The results are shown below in Table 3. The data demonstrates that the currently disclosed methods can form rings of differing size, and that the current methods are not limited to a predetermined number of amino acids or peptidic moieties to form cyclative release product.

TABLE 3

Cyclative Release

| | Sequence (Position N→C) | | | | | | | | Cyclative Release UV (214 nm) |
|---|---|---|---|---|---|---|---|---|---|
| Seq | 1 | 2 | 3 | 4 | 5 | 6 | 7 | 8 | 9 | Peak Area |
| 9 | Ala | Pro | D-Leu | Ala | Phe | | | | | 4.9 |
| 10 | Ala | Leu | Pro | Leu | Ala | Phe | | | | 10.0 |
| 11 | Ala | Leu | Ala | Pro | D-Leu | Ala | Phe | | | 19.8 |
| 12 | Ala | Leu | D-Ala | Leu | Pro | Leu | Ala | Phe | | 26.0 |
| 13 | Ala | Leu | D-Ala | Leu | Ala | Pro | D-Leu | Ala | Phe | 0.8 |

Example 11: Cyclative Release with Non-Natural Stereochemistry and N-Methyl Variants Peptidic units with 6 moieties were synthesized as described in Example 1. Amino acids with N-methyl groups and/or D-stereochemistry were incorporated into the peptidic unit during synthesis. After synthesis of the peptidic unit, the alkylation, deprotection, and cyclative release steps as described in Examples 3-6 were performed. After the cyclative release reaction, remaining peptidic units ("linear product") were cleaved from the resin with 20 equivalents of propyl amine. Cyclative release efficiency was calculated as described in Example 9.

The results are shown below in Table 4. The data demonstrates that non-natural amino acids can be incorporated into the peptidic unit without disrupting cyclative release efficiency.

TABLE 4

Cyclative Release efficiency

| | Sequence (Position N→C) | | | | | | Cyclative Release Efficiency |
|---|---|---|---|---|---|---|---|
| Seq | 1 | 2 | 3 | 4 | 5 | 6 | (%) |
| 14 | Ala | NMe-D-Ala | NMe-Leu | Leu | D-Pro | Leu | 93 |
| 15 | D-Ala | NMe-Ala | NMe-Leu | Leu | D-Pro | Leu | 95 |
| 16 | Phe | NMe-D-Ala | NMe-Leu | Leu | D-Pro | Leu | 91 |
| 17 | D-Phe | NMe-Ala | NMe-Leu | Leu | D-Pro | Leu | 91 |
| 18 | D-Ala | NMe-Ala | NMe-D-Leu | Leu | D-Pro | Leu | 98 |
| 19 | D-Ala | D-Ala | NMe-D-Leu | NMe-Leu | D-Pro | Leu | 64 |
| 20 | Ala | Leu | D-Ala | Pro | Tyr | Leu | 90 |
| 21 | Sar | Leu | D-Ala | Pro | Tyr | Leu | 89 |

Example 12: Cyclative Release with Peptoid Moieties, Non-Natural Stereochemistry and N-Methyl Variants Peptidic units with 6 moieties were synthesized as described in Example 2. Peptoid moieties (denoted "O—" in Table 5, below) and amino acids with N-methyl groups and/or D-stereochemistry were incorporated into the peptidic unit during synthesis. After synthesis of the peptidic unit, the alkylation, deprotection, and cyclative release steps as described in Examples 3-6 were performed. After the cyclative release reaction, remaining peptidic units ("linear product") were cleaved from the resin with 20 equivalents of propyl amine. Cyclative release efficiency was calculated as described in Example 9.

The results are shown below in Table 5. The data demonstrates that non-natural amino acids and amino acid surrogates (such as peptoids) can be incorporated into the peptidic unit without disrupting cyclative release efficiency.

TABLE 5

Cyclative Release efficiency

| | Sequence (Position N→C) | | | | | Linear Purity (%) | Cyclative Release Efficiency (%) |
|---|---|---|---|---|---|---|---|
| Seq 1 | 2 | 3 | 4 | 5 | 6 | | |
| 22 D-Pro | O-Phe[2] | Leu | D-Leu | Leu | Leu | 77 | 83 |
| 23 D-Pro | O-Phe[2] | Leu | NMe-D-Leu | NMe-Leu | Leu | 65 | 92 |
| 24 D-Pro | O-4Cl-Phe[1] | Leu | D-Leu | Leu | Leu | 72 | 93 |
| 25 D-Pro | O-4Cl-Phe[1] | Leu | NMe-D-Leu | NMe-Leu | Leu | 68 | 90 |
| 26 D-Pro | O-4Cl-Phe[1] | Leu | D-Leu | Leu | Phe | 52 | 100 |
| 27 D-Pro | O-4Cl-Phe[1] | Leu | NMe-D-Leu | NMe-Leu | Phe | 70 | 88 |
| 28 D-Phe | O-4Cl-Phe[1] | Leu | D-Leu | Leu | Leu | 82 | 88 |
| 29 D-Phe | O-4Cl-Phe[1] | Leu | NMe-D-Leu | NMe-Leu | Leu | 82 | 81 |
| 30 D-Pro | D-Ser | NMe-D-hhPhe[3] | NMe-Glu | O-4Cl-Phe[1] | Leu | 50 | 80 |
| 31 D-Pro | D-Ser | NMe-D-hhPhe[3] | NMe-Glu | O-Leu[2] | Leu | 58 | 100 |
| 32 D-Leu | NMe-D-Leu | O-Leu[2] | P | O-Phe[2] | Leu | 37 | 93 |
| 33 D-Leu | NMe-D-Leu | Sar[1] | P | O-4Cl-Phe[1] | Leu | 36 | 60 |

[1]Incorporated as Fmoc-AA.
[2]Incorporated in situ
[3]"hh" refers to "homohomo"; amino acids with two additional methylene units between the alpha carbon of the amino acid and its natural sidechain Linear purity is determined by the following process: A portion of the activated resin is cleaved with 20 equivalents propylamine in THF for three hours immediately following activation step. The solution is recovered, evaporated, and resuspended in 300 uL DMSO, and 2 μL of this solution is injected into the LCMS. Linear purity is calculated from the LCMS trace using the following equation: [(The UV(214 nm) peak corresponding to the product)/(Total UV(214 nm) peak area of species in the sample excluding that of the solvent front)]*100.

Example 13: Selective Deprotection and Sidechain-to-Tail Cyclative Release

Linear peptide synthesis was performed as described in Example 1. The cyclization amine (i.e. the amine that will act as the nucleophile in the cyclization reaction) is protected with 4-methyltrityl (MTT), all other amines, including the N-terminal amine are BOC protected (generically represented by Formula Vc)

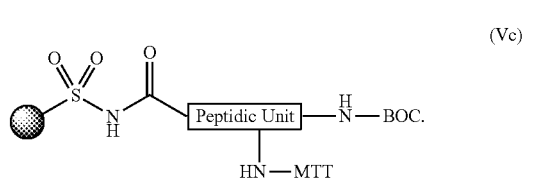

(Vc)

The peptidic units synthesized in the current example had N to C sequences of [Boc]-A-K(MTT)-A-P-L and [Boc]-A-K(MTT)-A-P-Y-L, where [BOC] represents the BOC protecting group covalently linked to the N-terminus. The structure of the peptidic unit on the solid-phase support after linear synthesis is shown below where the MTT protected lysine is shown as (—NH-MTT), the BOC protected N-terminus is shown as (—NH-BOC), and "L," "P,", "A," "K," and "Y" are the one letter abbreviation for amino acids.

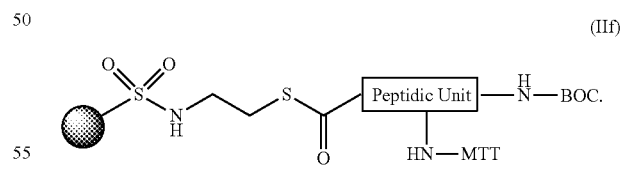

An alkylation and deprotection reaction is performed on each samples as described in Examples 3 and 4, providing a compound of Formula IIf (IIf)

Next, a selective deprotection reaction is performed to remove the MMT group, but not remove the BOC group. The resin containing the compound of Formula IIf was swelled in dry DCM. A solution of 3% TFA in dry DCM was added to the resin and the reaction mixture was shaken for 1 hour. After 1 hour, the resin was then washed with DCM (3×), THF (3×), DCM (3×).

After selective deprotection, a cyclative release reaction is performed as described in Example 6, providing a compound of Formula Ic.

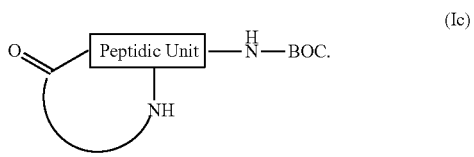

After the cyclative release reaction, remaining peptidic units ("linear product") were cleaved from the resin with 20 equivalents of propyl amine. Cyclative release efficiency was calculated as described in Example 9. The cyclative release efficiency of the [Boc]-A-K(Mtt)-A-P-L and [Boc]-A-K(Mtt)-A-P-Y-L compounds were between 20-30%.

The BOC group of Formula Ic is removed using the conditions described in Example 5, providing a compound of Formula Id

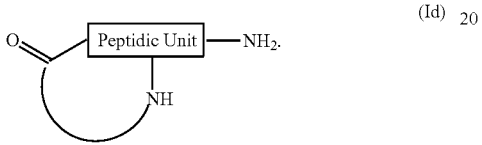

Example 14: Sidechain-to-Tail Cyclative Release

Linear peptide synthesis was performed as described in Example 1 except that the final amino acid added included a acylated N-terminus instead of a BOC protecting group. The peptidic unit prepared had an N to C sequence of: [Ac]-A-K(MTT)-A-P-L, where [Ac] represents the acyl group covalently linked to the N-terminus. The structure of the peptidic unit on the solid-phase support after linear synthesis is shown below where the MTT protected lysine is shown as (—NH-MTT), the acylated N-terminus is shown as (—NH—C(O)—CH₃), and "L," "P,", "A," and "K," are the one letter abbreviation for amino acids

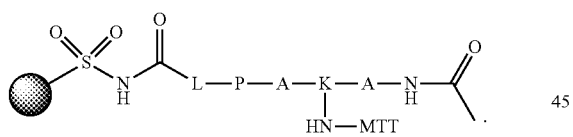

An alkylation and deprotection reaction is performed as described in Examples 3 and 4, providing a compound shown below

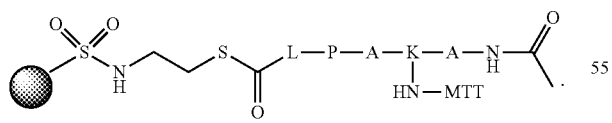

Next, a deprotection reaction is performed to remove the MTT group. The resin containing the peptidic unit shown above was swelled in dry DCM. A solution of 3% TFA in dry DCM was added to the resin and the reaction mixture was shaken for 1 hour. After 1 hour, the resin was then washed with DCM (3×), THF (3×), DCM (3×).

After deprotection, a cyclative release reaction is performed as described in Example 6, providing a compound as shown below:

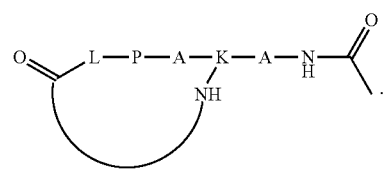

After the cyclative release reaction, remaining peptidic units ("linear product") were cleaved from the resin with 20 equivalents of propyl amine. Cyclative release efficiency was calculated as described in Example 9. The cyclative release efficiency of the above compound was about 50%

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing a cyclized peptidic compound of Formula

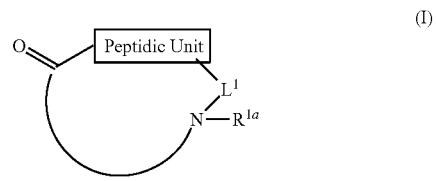

the method comprising
forming a cyclization reaction mixture comprising a thiophilic catalyst, a non-nucleophilic base, and a compound of Formula II:

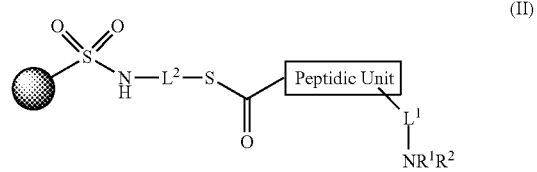

under conditions suitable to form the cyclized peptidic compound of Formula I, wherein
⬤ is a solid-phase support;
$R^{1a}$ is selected from the group consisting of H, $NH_2$, $C_{1-8}$ alkyl, and $C_{3-8}$ cycloalkyl;
$L^1$ is selected from the group consisting of a bond, N—H, and —O—,
provided that when $R^{1a}$ is $NH_2$, then $L^1$ is a bond; and
provided that when $L^1$ is —O—, then $R^{1a}$ is H, $C_{1-8}$ alkyl, or $C_{3-8}$ cycloalkyl;
$R^1$ is selected from the group consisting of H, $NH_2$, $C_{1-8}$ alkyl, and $C_{3-8}$ cycloalkyl,
provided than when $R^1$ is $NH_2$, then $L^1$ is a bond;

R² is H;
L² is selected from the group consisting of $C_{2-8}$ alkylene, $C_{3-8}$ cycloalkylene, 3- to 8-membered heterocycloalkylene, $C_{6-10}$ arylene, and 5- to 10-membered heteroarylene, each of which is optionally substituted with from 1 to 4 substituents selected from the group consisting of $C_{1-4}$ alkyl, cyano, —C(O)R$^a$, —C(O)OR$^a$, —SR$^a$, —$C_{1-4}$alkyl-SR$^a$, and oxo, wherein the heterocycoalkylene and heteroarylene each have from 1 to 3 heteroatom ring members each independently selected from the group consisting of N, O and S; and
R$^a$ is selected from the group consisting of H and $C_{1-8}$ alkyl.

2. The method of claim 1, wherein the thiophilic catalyst is a metal thiophilic catalyst.

3. The method of claim 2, wherein the metal thiophilic catalyst is selected from the group consisting of copper, nickel, mercury, silver, ruthenium, osmium, and strontium.

4. The method of claim 3, wherein the metal thiophilic catalyst is silver.

5. The method of claim 1, wherein the non-nucleophilic base is an amine non-nucleophilic base.

6. The method of claim 5, wherein the amine non-nucleophilic base is selected from the group consisting of trimethylamine, triethylamine, diisopropylethylamine (DIPEA), 1,8-diazabicycloundec-7-ene (DBU), 2,6-di-tert-butylpyridine, and quinuclidine.

7. The method of claim 6, wherein the amine non-nucleophilic base is DIPEA.

8. The method of claim 1, wherein R¹ is H.

9. The method of claim 1, wherein R¹ is NH₂.

10. The method of claim 1, wherein L¹ is a bond.

11. The method of claim 1, wherein R$^{1a}$ is H.

12. The method of claim 1, wherein the Peptidic Unit has the structure:

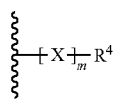

wherein,
m is an integer from 2 to 10;
each X is independently selected from the group consisting of $C_{3-8}$ cycloalkylene, X¹—$C_{3-8}$ cycloalkylene, heterocycloalkylene, X¹-heterocycloalkylene, $C_{6-10}$ arylene, —X¹—$C_{6-10}$ arylene, heteroarylene, —X¹-heteroarylene,

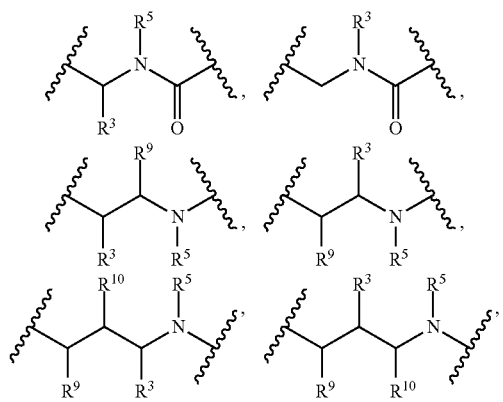

wherein each heterocycoalkylene comprises from 3 to 8 ring members having 1 to 3 heteroatom ring members, each independently selected from N, O and S, and each heteroarylene comprises from 5 to 10 ring members having 1 to 3 heteroatom ring members, each independently selected from the group consisting of N, O and S,
wherein
each Y is independently selected from the group consisting of CH₂, NR⁵, O, S, S(O), and S(O)₂;
each n is an integer from 1 to 8;
each R³ is independently selected from the group consisting of H, halogen, cyano, $C_{1-8}$ alkyl, $C_{2-8}$ alkenyl, $C_{2-8}$ alkynyl, $C_{1-8}$ haloalkyl, —OR$^d$, —X¹—OR$^d$, —SR$^b$, —X¹—SR$^b$, —NR$^b$R$^d$, —X¹—NR$^b$R$^d$, (O)R$^b$—X¹—C(O)R$^b$, —C(O)OR$^b$, —X¹—C(O)OR$^b$, —C(O)NR$^b$R$^c$, —X¹—C(O)NR$^b$R$^c$, —OC(O)NR$^b$R$^c$, —X¹—OC(O)NR$^b$R$^c$, —NR$^b$C(O)R$^c$, —X¹—NR$^b$R$^c$ (O)R$^c$, —NR$^b$C(O)₂R$^c$, —X¹—NR$^b$C(O)₂R$^c$, —NR$^b$C(O) NR$^b$R$^c$, —X¹—NR$^b$C(O)NR$^b$R$^c$, —S(O)₂NR$^b$R$^c$, —$X^1$—$S(O)_2NR^aR^b$, —$NR^bC(NH)NR^bR^c$, —$X^1$—$NR^b(NH)NR^bR^c$, $C_{3-8}$ cycloalkyl, $X^1$—$C_{3-8}$ cycloalkyl, $C_{6-10}$ aryl, —$X^1$—$C_{6-10}$aryl, heterocycloalkyl, —$X^1$-heterocycloalkyl, heteroaryl, and —$X^1$-heteroaryl, wherein the $C_{3-8}$ cycloalkyl, $C_{6-10}$ aryl, heterocycloalkyl, and heteroaryl moieties are optionally substituted with 1 to 4 substituents each independently selected from the group consisting of $C_{1-4}$ alkyl, halogen, cyano, —$OR^b$, —$X^1$—$OR^b$, —$SR^b$, —$X^1$—$SR^b$, —$NR^bR^d$, and —$X^1$—$NR^bR^d$, each heterocycloalkyl comprises from 3 to 8 ring members having 1 to 3 heteroatom ring members each independently selected from the group consisting of N, O and S, and each heteroaryl comprises 5 to 10 ring members having 1 to 3 heteroatom ring members each independently selected from the group consisting of N, O and S;

$R^4$ is selected from the group consisting of H, $C_{1-8}$ alkyl, —$OR^d$, —$NR^bR^d$, —$[C(H)(R^3)]_{1-6}$ $NR^bR^d$, —$X^1$—$C(O)R^b$, $C(O)R^b$, NH—$C(O)R^b$, $C(O)OR^b$, —$X^1$—$C(O)OR^b$, —$C(O)NR^bR^c$, and $C_{3-8}$ cycloalkyl;

each $R^5$ is independently selected from the group consisting of H and $C_{1-8}$ alkyl;

alternatively, $R^3$ and $R^5$ within the same X unit are combined with the atoms to which they are attached to form a 5- to 6-membered heterocycloalkyl ring having from 1 to 3 additional heteroatoms each independently selected from the group consisting of N, O and S, the 5- to 6-membered heterocycloalkyl ring is optionally further substituted with from 1 to 3 substituents independently selected from the group consisting of halogen, cyano, $C_{1-8}$ alkyl, $C_{2-8}$ alkenyl, $C_{2-8}$ alkynyl, $C_{1-8}$ haloalkyl, —$OR^b$, —$X^1$—$OR^b$, —$SR^b$, —$X^1$—$SR^b$, —$NR^bR^d$, —$X^1$—$NR^bR^d$, $C(O)R^b$, —$X^1$—$C(O)R^b$, —$C(O)OR^b$, —$X^1$—$C(O)OR^b$, —$C(O)NR^bR^c$, —$X^1$—$C(O)NR^bR^c$, —$NR^bC(O)R^c$, —$X^1$—$NR^bC(O)R^c$, —$NR^bC(O)_2R^c$, —$X^1$—$NR^bC(O)_2R^c$, —$S(O)_2NR^bR^c$, or —$X^1$—$S(O)_2NR^aR^b$;

$R^{6a}$ and $R^{6b}$ are each independently selected from the group consisting of H and halogen;

$R^9$ and $R^{10}$ are each independently selected from the group consisting of H, $C_{1-8}$ alkyl, and OH;

each $X^1$ is independently $C_{1-6}$alkylene;

each $R^b$ and $R^c$ is independently selected from the group consisting of H, $C_{1-8}$ alkyl, and $C_{1-8}$ haloalkyl; and each $R^d$ is independently selected from the group consisting of H, $C_{1-8}$alkyl, $C_{1-8}$ haloalkyl, and $NH_2$.

13. The method of claim 12, wherein each X has the structure selected from the group consisting of:

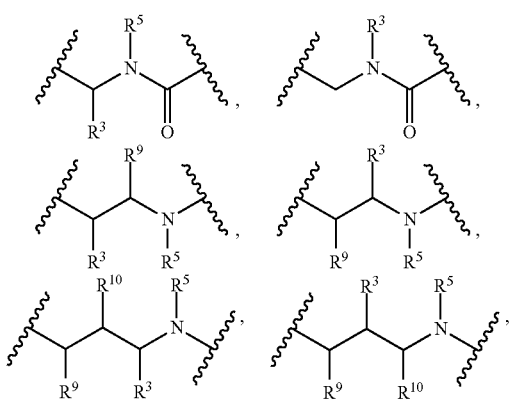

14. The method of claim 12, wherein each X has the structure selected from the group consisting of:

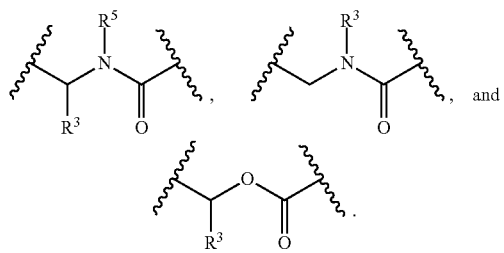

15. The method of claim 12, wherein the peptidic unit includes at least one natural amino acid.

16. The method of claim 1, wherein $L^2$ has a structure:

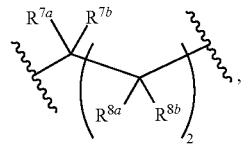

wherein, q is an integer from 1 to 3; and $R^{7a}$, $R^{7b}$ and each $R^{8a}$, and $R^{8b}$ are independently selected from the group consisting of H, $C_{1-4}$alkyl, cyano, —$C(O)R^a$, —$C(O)OR^a$, —$C_{1-4}$alkyl-$SR^a$, —$SR^a$, and oxo;

alternatively, $R^{7b}$ and $R^{8a}$ are combined with the atoms to which they are attached to form a member selected from the group consisting of $C_{3-8}$ cycloalkyl, $C_{6-10}$ aryl, 3- to 8-membered heterocycloalkyl, and 5- to 10-membered heteroaryl, wherein the heterocycloalkyl and heteroaryl groups each have from 1 to 3 heteroatom ring members each independently selected from the group consisting of N, O and S.

17. The method of claim 16, wherein q is 1.

18. The method of claim 16, wherein $R^{7a}$, $R^{7b}$ and each $R^{8a}$, and $R^{8b}$ are independently selected from the group consisting of H, $C_{1-4}$alkyl, and —$SR^a$.

19. The method of claim 16, wherein $R^{7a}$, $R^{7b}$, and each $R^{8a}$, and $R^{8b}$ are H.

20. The method of claim 1, wherein the compound of Formula II has the structure of Formula IIa:

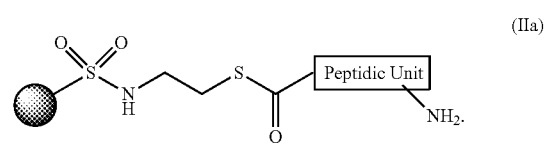

21. The method of claim 1, wherein the compound of Formula I has the structure of Formula Ia:

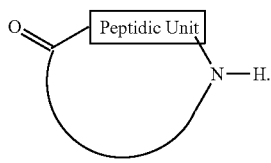
(Ia)

22. The method of claim 1, further comprising forming a transfer reaction mixture comprising the compound of Formula III:

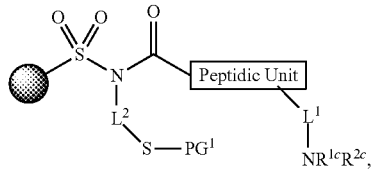
(III)

and a first acid under conditions suitable to form an intermediate of Formula IV:

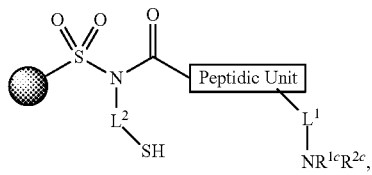
(IV)

wherein the intermediate of Formula IV undergoes an N- to S-acyl transfer reaction to form a compound of Formula IIb:

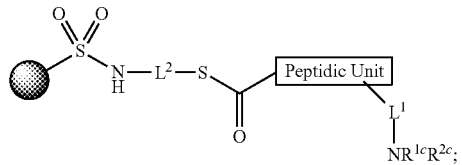
(IIb)

and
forming a deprotection reaction mixture comprising the compound of Formula IIb and a second acid under conditions suitable to form the compound of Formula II,
wherein
PG$^1$ is a mercapto protecting group;
R$^{1c}$ is selected from the group consisting of NH—PG$^2$, H, C$_{1-8}$ alkyl, and C$_{3-8}$ cycloalkyl;
provided that when R$^{1c}$ is NH$_2$, then L$^1$ is a bond; and
provided that when L$^1$ is —O—, then R$^{1c}$ is H, C$_{1-8}$ alkyl, or C$_{3-8}$ cycloalkyl;
R$^{2c}$ is selected from the group consisting of PG$^2$ and H,
provided that when R$^{2c}$ is H, then R$^{1c}$ is NH—PG$^2$, and provided that when R$^{2c}$ is PG$^2$, then R$^{1c}$ is H, C$_{1-8}$ alkyl, or C$_{3-8}$ cycloalkyl; and
PG$^2$ is an amine protecting group.

23. The method of claim 1, further comprising forming a transfer/deprotection reaction mixture comprising the compound of Formula III:

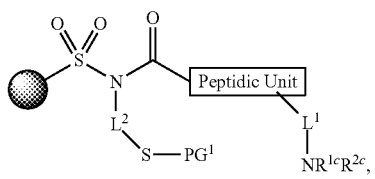
(III)

and an acid under conditions suitable to form an intermediate of Formula IVa:

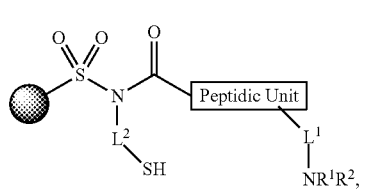
(IVa)

wherein the intermediate of Formula IVa undergoes an N- to S-acyl transfer reaction to form a compound of Formula II:

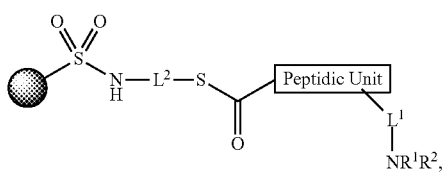
(II)

wherein
PG$^1$ is a mercapto protecting group;
R$^{1c}$ is selected from the group consisting of NH—PG$^2$, H, C$_{1-8}$ alkyl, and C$_{3-8}$ cycloalkyl;
provided that when R$^{1c}$ is NH$_2$, then L$^1$ is a bond; or
provided that when L$^1$ is —O—, then R$^{1c}$ is H, C$_{1-8}$ alkyl, or C$_{3-8}$ cycloalkyl;
R$^{2c}$ is selected from the group consisting of PG$^2$ and H,
provided that when R$^{2c}$ is H, then R$^{1c}$ is NH—PG$^2$, or
provided that when R$^{2c}$ is PG$^2$, then R$^{1c}$ is H, C$_{1-8}$ alkyl, or C$_{3-8}$ cycloalkyl; and
PG$^2$ is an amine protecting group.

24. The method of claim 22, further comprising:
forming a coupling reaction mixture comprising the compound of Formula V:

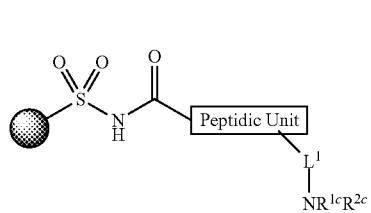

(V)

and a compound of Formula VI:

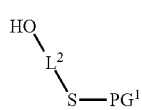

(VI)

under Mitsunobu reaction conditions to form the compound of Formula III.

25. The method of claim 1, wherein the compound of Formula I has the structure of Formula Ia:

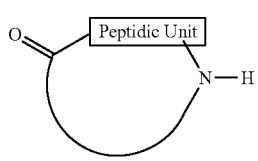

(Ia)

the method comprising
i) forming a coupling reaction mixture comprising a compound of Formula Va:

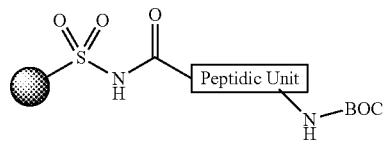

(Va)

and triisopropylsilyl (TIPS)-protected mercaptoethanol under Mitsunobu reaction conditions to form a compound of Formula IIIa:

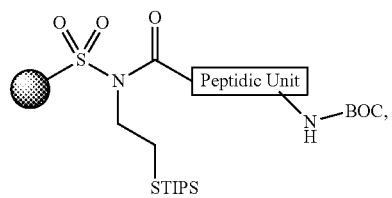

(IIIa)

ii) forming a transfer reaction mixture comprising the compound of Formula IIIa, acetic acid, and tetra-N-butylammonium fluoride (TBAF) under conditions suitable to form an intermediate of Formula IVb:

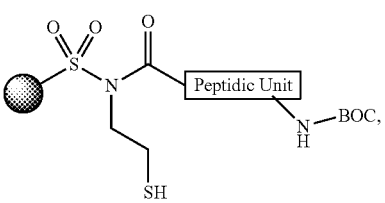

(IVb)

wherein the intermediate of Formula IVb undergoes an N- to S-acyl transfer reaction to form a compound of Formula IIc:

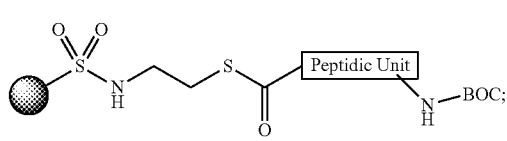

(IIc)

iii) forming a deprotection reaction mixture comprising the compound of Formula IIc and trifluoroacetic acid (TFA) to form a compound of Formula IIa:

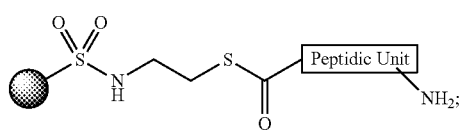

(IIa)

iv) forming a cyclization reaction mixture comprising silver, N,N-diisopropylethylamine (DIPEA), and the compound of Formula IIa under conditions suitable to form the cyclized peptidic compound of Formula Ia.

26. A method for preparing a cyclized peptidic compound comprising
forming a reaction mixture comprising a metal thiophilic catalyst, a non-nucleophilic base and a linear peptidic compound covalently linked to a solid-phase support via a linker, under conditions suitable to form the cyclized peptidic compound and cleave the cyclized peptidic compound from the solid-phase support,
wherein the linear peptidic compound is covalently linked to the linker via a thioester moiety, and wherein the linker is covalently linked to the solid-phase support via a sulfonamide moiety, such that cyclization and cleavage of the linear peptidic compound cleaves the thioester moiety to form an amide.

* * * * *